(12) United States Patent
Huelskamp et al.

(10) Patent No.: US 9,656,091 B2
(45) Date of Patent: May 23, 2017

(54) POWER SAVING COMMUNICATION FOR MEDICAL DEVICES

(71) Applicant: CARDIAC PACEMAKERS, INC., St. Paul, MN (US)

(72) Inventors: Paul Huelskamp, St. Paul, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/793,270

(22) Filed: Jul. 7, 2015

(65) Prior Publication Data

US 2016/0007873 A1 Jan. 14, 2016

Related U.S. Application Data

(60) Provisional application No. 62/023,585, filed on Jul. 11, 2014.

(51) Int. Cl.
*A61N 1/372* (2006.01)
*A61B 5/0452* (2006.01)
(Continued)

(52) U.S. Cl.
CPC ........ *A61N 1/37276* (2013.01); *A61B 5/0452* (2013.01); *A61B 5/686* (2013.01);
(Continued)

(58) Field of Classification Search
CPC ....... A61B 5/0452; A61B 5/686; A61B 5/046; A61B 5/0464; A61B 5/0472; A61B 5/7275; A61B 2560/0209; A61N 1/37256; A61N 1/3622; A61N 1/3625; A61N 1/3684; A61N 1/3708; A61N 1/37205; A61N 1/37288; A61N 1/3756; A61N 1/3956
(Continued)

(56) References Cited

U.S. PATENT DOCUMENTS 6,441,747 B1 * 8/2002 Khair ................... A61B 5/0006
128/903
7,587,241 B2 9/2009 Parramon et al.
(Continued)

*Primary Examiner* — Michael Carey
(74) *Attorney, Agent, or Firm* — Seager, Tufte & Wickhem LLP

(57) ABSTRACT

Power saving communication techniques for communicating in a medical device system. One example medical device system may be for delivering electrical stimulation therapy to a heart of a patient, and may include a first implantable medical device implanted in a first chamber of the heart and configured to determine one or more parameters, a medical device physically spaced from and communicatively coupled to the first implantable medical device, the medical device configured to deliver electrical stimulation therapy to the heart of the patient, wherein the first implantable medical device is further configured to: compare a value of a first determined parameter to a first threshold; if the value of the first determined parameter passed the first threshold, communicate a first indication to the medical device; and if the value of the first determined parameter has not passed the first threshold, not communicating the first indication to the medical device.

17 Claims, 12 Drawing Sheets

(51) Int. Cl.
*A61B 5/00* (2006.01)
*A61N 1/375* (2006.01)
*A61N 1/39* (2006.01)
*A61B 5/046* (2006.01)
*A61B 5/0464* (2006.01)
*A61B 5/0472* (2006.01)
*A61N 1/362* (2006.01)
*A61N 1/368* (2006.01)
*A61N 1/37* (2006.01)

(52) U.S. Cl.
CPC .............. *A61B 5/046* (2013.01); *A61B 5/0464* (2013.01); *A61B 5/0472* (2013.01); *A61B 5/7275* (2013.01); *A61B 2560/0209* (2013.01); *A61N 1/3622* (2013.01); *A61N 1/3625* (2013.01); *A61N 1/3684* (2013.01); *A61N 1/3708* (2013.01); *A61N 1/3756* (2013.01); *A61N 1/37205* (2013.01); *A61N 1/37288* (2013.01); *A61N 1/3956* (2013.01)

(58) Field of Classification Search
USPC ............... 607/32, 60, 62; 600/509, 527, 528
See application file for complete search history.

(56) References Cited

U.S. PATENT DOCUMENTS

| | | | |
|---|---|---|---|
| 7,957,813 B1 | 6/2011 | Persson et al. | |
| 8,374,693 B2 | 2/2013 | Chavan et al. | |
| 8,401,659 B2 | 3/2013 | Von Arx et al. | |
| 8,554,333 B2 | 10/2013 | Wu et al. | |
| 8,571,678 B2 | 10/2013 | Wang | |
| 8,700,173 B2 | 4/2014 | Edlund | |
| 8,744,572 B1 | 6/2014 | Greenhut et al. | |
| 2004/0153127 A1* | 8/2004 | Gordon | A61N 1/3601 607/1 |
| 2006/0136004 A1* | 6/2006 | Cowan | A61N 1/37205 607/33 |
| 2006/0265018 A1 | 11/2006 | Smith et al. | |
| 2009/0063187 A1* | 3/2009 | Johnson | A61B 5/0022 705/2 |
| 2011/0184491 A1 | 7/2011 | Kivi | |
| 2012/0221067 A1* | 8/2012 | Edlund | A61B 5/0006 607/7 |
| 2012/0229299 A1 | 9/2012 | Skoldengen et al. | |
| 2012/0290025 A1* | 11/2012 | Keimel | A61N 1/3756 607/3 |
| 2013/0041422 A1 | 2/2013 | Jacobson | |
| 2013/0079861 A1* | 3/2013 | Reinert | A61N 1/3756 607/126 |
| 2014/0058240 A1* | 2/2014 | Mothilal | A61N 1/37205 600/381 |
| 2014/0107734 A1 | 4/2014 | Park et al. | |
| 2014/0214104 A1 | 7/2014 | Greenhut et al. | |
| 2015/0142069 A1* | 5/2015 | Sambelashvili | A61N 1/3688 607/18 |

\* cited by examiner

# POWER SAVING COMMUNICATION FOR MEDICAL DEVICES

CROSS-REFERENCE TO RELATED APPLICATIONS

This application claims priority under 35 U.S.C. §119 to U.S. Provisional Application Ser. No. 62/023,585, filed Jul. 11, 2014, the entirety of which is incorporated herein by reference.

TECHNICAL FIELD

The present disclosure generally relates to systems, devices, and methods for communicating information, and more particularly, to systems, devices, and methods for communicating information between medical devices in a power efficient manner.

BACKGROUND

Pacing instruments can be used to treat patients suffering from various heart conditions that may result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, a patient may have multiple implanted devices that are configured to communicate information between the devices.

SUMMARY

The present disclosure generally relates to systems, devices, and methods for communicating information, and more particularly, to systems, devices, and methods for communicating information between medical devices for detecting and treating cardiac arrhythmias.

In a first example, a medical device system for delivering electrical stimulation therapy to a heart of a patient may comprise a first implantable medical device configured to be implanted in a first chamber of the heart and configured to determine one or more parameters, a medical device physically housed separately from and communicatively coupled to the first implantable medical device, the medical device configured to deliver electrical stimulation therapy to the heart of the patient, wherein the first implantable medical device is further configured to: compare a value of a first determined parameter to a first threshold; and if the value of the first determined parameter passed the first threshold, communicate a first indication to the medical device; and if the value of the first determined parameter has not passed the first threshold, not communicating the first indication to the medical device.

Alternatively, or additionally, in any of the above examples, the first indication may comprise the value of the first determined parameter.

Alternatively, or additionally, in any of the above examples, after communicating the first indication to the medical device, the first implantable medical device may be configured to: compare the value of the first determined parameter to a second threshold, where the second threshold is different from the first threshold; if the value of the first determined parameter passed the second threshold, communicate a second indication to the medical device; and if the value of the first determined parameter has not passed the second threshold, not communicating the second indication to the medical device.

Alternatively, or additionally, in any of the above examples, the second threshold is higher than the first threshold.

Alternatively, or additionally, in any of the above examples, the second threshold is lower than the first threshold.

Alternatively, or additionally, in any of the above examples, the medical device may communicate a delta value to the first implantable medical device, and wherein the first implantable medical device adds the delta value to the first threshold to arrive at the second threshold. The delta value may be positive or negative in value.

Alternatively, or additionally, in any of the above examples, the first predetermined parameter may correspond to a heart rate, a QRS width, an A-V interval, a V-V interval, or a T-wave amplitude.

Alternatively, or additionally, in any of the above examples, the first implantable medical device comprises a leadless pacemaker (LCP).

Alternatively, or additionally, in any of the above examples, the first implantable medical device comprises a leadless pacemaker (LCP) and the medical device comprises a second implantable medical device.

Alternatively, or additionally, in any of the above examples, the second implantable medical device comprises one of: an implantable cardioverter-defibrillator (ICD); an implantable subcutaneous cardioverter-defibrillator (S-ICD); and an implantable cardiac pacemaker (ICP).

Alternatively, or additionally, in any of the above examples, the medical device comprises an external medical device.

Alternatively, or additionally, any of the above examples may further comprise a second implantable medical device implanted in a second chamber of the heart, the second implantable medical device configured to sense cardiac events in the second chamber of the heart and communicate information related to the sensed cardiac events to the first implantable medical device, wherein the first implantable medical device is further configured to: sense cardiac events in the first chamber of the heart, and determine a difference in timings between the sensed cardiac events in the second chamber of the heart and the sensed cardiac events in the first chamber of the heart, and wherein the one or more parameters comprises a delay between the sensed cardiac events in the second chamber of the heart and the sensed cardiac events in the first chamber of the heart.

Alternatively, or additionally, in any of the above examples, the first chamber of the heart is an atrium and the second chamber of the heart is a ventricle, and the delay between the sensed cardiac events in the second chamber of the heart and the sensed cardiac events in the first chamber of the heart may correspond to an A-V delay.

Alternatively, or additionally, in any of the above examples, the medical device may communicate the first threshold to the first implantable medical device.

Alternatively, or additionally, in any of the above examples, after the first implantable medical device communicates a first indication to the medical device, the medical device may be configured to communicate an acknowledgement to the first implantable medical device, and if the first implantable medical device does not receive the acknowledgement from the medical device within a predetermined period of time, the first implantable medical device may be further configured to communicate the first indication to the medical device again.

Alternatively, or additionally, in any of the above examples, the predetermined period of time is between two-hundred fifty milliseconds (250 ms) and one second (1 s).

Alternatively, or additionally, in any of the above examples, the first implantable medical device may be further configured to: compare a second determined parameter to another threshold; if the value of the second determined parameter of the patient has passed the another threshold, communicate another indication to the medical device; and if the value of the second determined parameter of the patient has not passed the another threshold, not communicating the another indication to the medical device.

In another example, a method of communicating information from a first medical device to a second medical device may comprise communicating a first threshold corresponding to a first physiological parameter of a patient from a first medical device to a second medical device, wherein the second medical device is implanted within the patient, monitoring a value of the first physiological parameter of the patient with the second medical device, determining if the value of the first physiological parameter of the patient has passed the first threshold, if the value of the first physiological parameter of the patient has passed the first threshold, communicating a first indication from the second medical device to the first medical device, and if the value of the first physiological parameter of the patient has not passed the first threshold, not communicating the first indication from the second medical device to the first medical device.

Alternatively, or additionally, in any of the above examples, the first indication may comprise the value of the first physiological parameter.

Alternatively, or additionally, in any of the above examples, the first medical device comprises a leadless pacemaker (LCP) and the second medical device comprises a subcutaneous implantable cardioverter-defibrillator (S-ICD).

Alternatively, or additionally, in any of the above examples, the first physiological parameter corresponds to a heart rate, a QRS width, an A-V interval, a V-V interval, or a T-wave amplitude.

Alternatively, or additionally, any of the above examples may further comprise after communicating the first indication from the second medical device to the first medical device, communicating a second threshold corresponding to the first physiological parameter of the patient from the first medical device to the second medical device, wherein the second threshold is different from the first threshold; monitoring the value of the first physiological parameter of the patient with the second medical device; and determining if the value of the first physiological parameter of the patient has passed the second threshold; if the value of the first physiological parameter of the patient has passed the second threshold, communicating a second indication from the second medical device to the first medical device; and if the value of the first physiological parameter of the patient has not passed the second threshold, not communicating the second indication from the second medical device to the first medical device.

Alternatively, or additionally, in any of the above examples, communicating the second threshold may comprise communicating a new first threshold value from the first medical device to the second medical device.

Alternatively, or additionally, in any of the above examples, communicating the second threshold may comprise communicating a delta value from the first medical device to the second medical device, wherein the second medical device adds the delta value to the first threshold to arrive at the second threshold.

Alternatively, or additionally, any of the above examples may further comprise communicating another threshold corresponding to a second physiological parameter of a patient from a first medical device to the second medical device, monitoring a value of the second physiological parameter of the patient with the second medical device, and determining if the value of the second physiological parameter of the patient has passed the another threshold, if the value of the second physiological parameter of the patient has passed the another threshold, communicating another indication from the second medical device to the first medical device, and if the value of the second physiological parameter of the patient has not passed the another threshold, not communicating the another indication from the second medical device to the first medical device.

Alternatively, or additionally, any of the above examples may further comprise after communicating the first indication from the second medical device to the first medical device, communicating an acknowledgement from the first medical device to the second medical device, and if the second medical device does not receive the acknowledgement from the first medical device within a predetermined period of time, communicating the first indication from the second medical device to the first medical device again.

Alternatively, or additionally, in any of the above examples, the predetermined period of time is between two-hundred fifty milliseconds (250 ms) and one second (1 s).

In yet another example, a medical device system for delivering electrical stimulation therapy to a heart of a patient may comprise a first implantable medical device implanted in a first chamber of the heart and configured to determine one or more parameters, a medical device physically spaced from and communicatively coupled to the first implantable medical device, the medical device configured to deliver electrical stimulation therapy to the heart of the patient, wherein the first implantable medical device is further configured to: compare a value of a first determined parameter to a first threshold; and if the value of the first determined parameter passed the first threshold, communicate a first indication to the medical device; and if the value of the first determined parameter has not passed the first threshold, not communicating the first indication to the medical device.

Alternatively, or additionally, in any of the above examples, the first indication may comprise the value of the first determined parameter.

Alternatively, or additionally, in any of the above examples, after communicating the first indication to the medical device, the first implantable medical device may be configured to: compare the value of the first determined parameter to a second threshold, where the second threshold is different from the first threshold; if the value of the first determined parameter passed the second threshold, communicate a second indication to the medical device; and if the value of the first determined parameter has not passed the second threshold, not communicating the second indication to the medical device.

Alternatively, or additionally, in any of the above examples, the first determined parameter corresponds to a heart rate, a QRS width, an A-V interval, a V-V interval, or a T-wave amplitude.

Alternatively, or additionally, any of the above examples may further comprise a second implantable medical device implanted in a second chamber of the heart, the second implantable medical device configured to sense cardiac events in the second chamber of the heart and communicate information related to the sensed cardiac events to the first implantable medical device, wherein the first implantable medical device is further configured to: sense cardiac events in the first chamber of the heart, and determine a difference in timings between the sensed cardiac events in the second chamber of the heart and the sensed cardiac events in the first chamber of the heart, and wherein the one or more parameters comprises a delay between the sensed cardiac events in the second chamber of the heart and the sensed cardiac events in the first chamber of the heart.

Alternatively, or additionally, in any of the above examples, the first chamber of the heart is an atrium and the second chamber of the heart is a ventricle, and the delay between the sensed cardiac events in the second chamber of the heart and the sensed cardiac events in the first chamber of the heart corresponds to an A-V delay.

In another example, a method of reducing communication transmissions in a medical device system may comprise: monitoring a parameter with an implantable leadless cardiac pacemaker; with the implantable leadless cardiac pacemaker, comparing the monitored parameter to a first threshold and determining if the value of the monitored parameter has passed the first threshold; if the value of the monitored parameter has passed the first threshold, communicating the value of the monitored parameter from the implantable leadless cardiac pacemaker to a subcutaneous implantable cardioverter-defibrillator (S-ICD); and if the value of the monitored parameter has not passed the first threshold, not communicating the value of the monitored parameter from the implantable leadless cardiac pacemaker to the subcutaneous implantable cardioverter-defibrillator (S-ICD).

Alternatively, or additionally, any of the above examples, may further comprise: after receiving the value of the monitored parameter at the subcutaneous implantable cardioverter-defibrillator (S-ICD), communicating a second threshold from the subcutaneous implantable cardioverter-defibrillator (S-ICD) to the implantable leadless cardiac pacemaker, wherein the second threshold is different from the first threshold; and if the value of the monitored parameter has passed the second threshold, communicating the value of the monitored parameter from the implantable leadless cardiac pacemaker to the subcutaneous implantable cardioverter-defibrillator (S-ICD); and if the value of the monitored parameter has not passed the second threshold, not communicating the value of the monitored parameter from the implantable leadless cardiac pacemaker to the subcutaneous implantable cardioverter-defibrillator (S-ICD).

Alternatively, or additionally, any of the above examples, may further comprise: after communicating the value of the monitored parameter from the implantable leadless cardiac pacemaker to the subcutaneous implantable cardioverter-defibrillator (S-ICD), communicating an acknowledgement from the subcutaneous implantable cardioverter-defibrillator (S-ICD) to the implantable leadless cardiac pacemaker; and if the implantable leadless cardiac pacemaker does not receive the acknowledgement from the subcutaneous implantable cardioverter-defibrillator (S-ICD) within a predetermined period of time, communicating the value of the monitored parameter from the implantable leadless cardiac pacemaker to the subcutaneous implantable cardioverter-defibrillator (S-ICD) again.

Alternatively, or additionally, in any of the above examples, the second threshold is higher than the first threshold.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
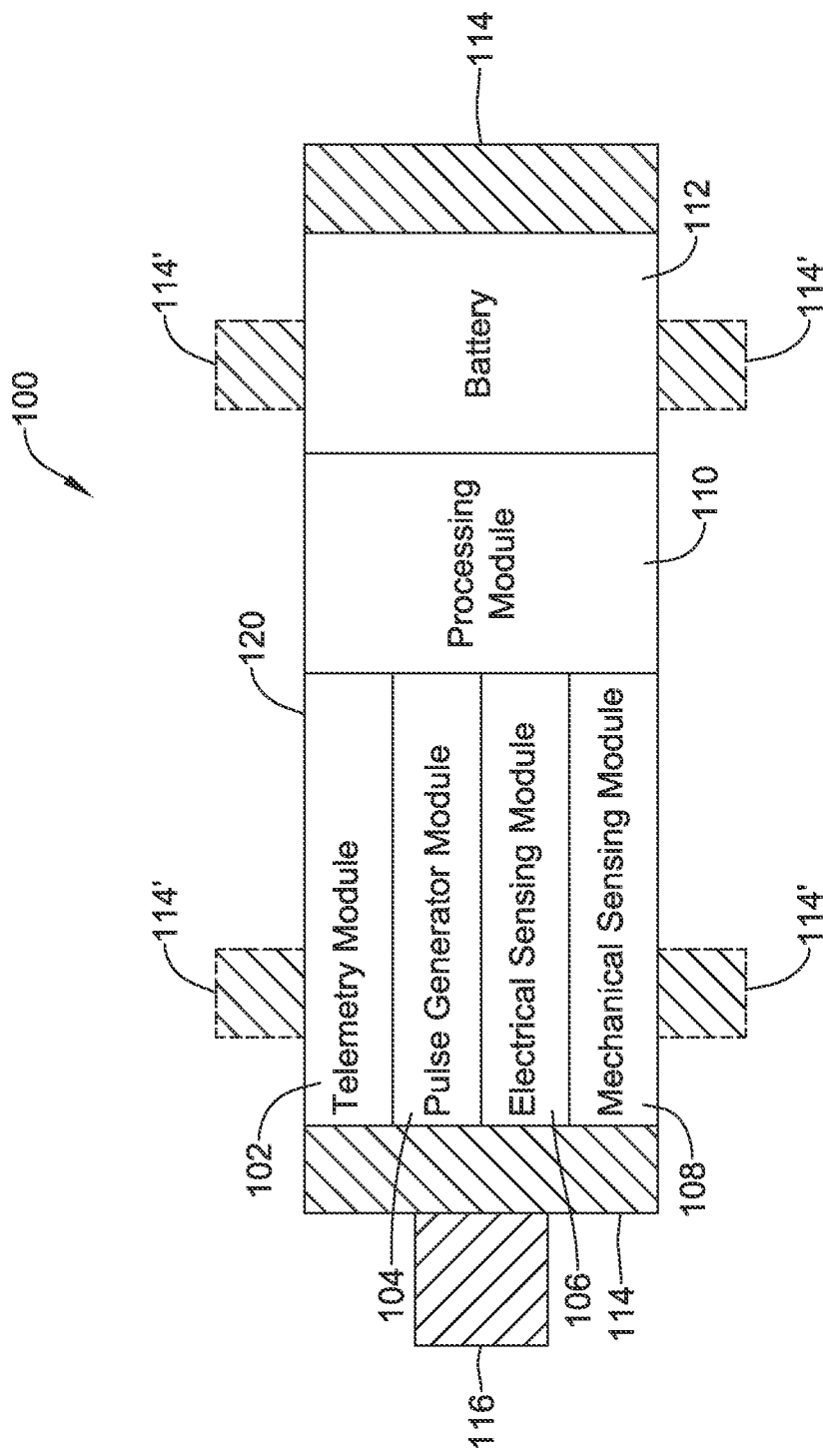
FIG. 1 is a schematic block diagram of an illustrative leadless cardiac pacemaker (LCP) according to one example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. In some examples, diseased cardiac tissues conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate. In some cases such an abnormality can develop into a fibrillation state, where the contraction of the patient's heart chambers are almost completely de-synchronized and the heart pumps very little to no blood. Implantable medical device which may be configured to determine occurrences of such cardiac abnormalities or arrhythmias and deliver one or more types of electrical stimulation therapy to patient's hearts may help to terminate or alleviate such cardiac conditions.

FIG. 1 depicts an exemplary leadless cardiac pacemaker (LCP) that may be implanted into a patient and may operate to prevent, control, or terminate cardiac arrhythmias in patients, for example by appropriately employing one or more therapies (e.g. anti-tachycardia pacing (ATP) therapy, cardiac resynchronization therapy (CRT), bradycardia therapy, defibrillation pulses, or the like). As can be seen in FIG. 1, LCP 100 may be a compact device with all components housed within LCP 100 or directly on housing 120. In the example shown in FIG. 1, LCP 100 may include a telemetry module 102, a pulse generator module 104, an electrical sensing module 106, a mechanical sensing module 108, a processing module 110, a battery 112, and electrodes 114. LCP 100 may include more of less modules, depending on the application.

Telemetry module 102 may be configured to communicate with devices such as sensors, other medical devices, and/or the like, that are located externally to LCP 100. Such devices may be located either external or internal to the patient's body. Irrespective of the location, external devices (i.e. external to the LCP 100 but not necessarily external to the patient's body) can communicate with LCP 100 via telemetry module 102 to accomplish one or more desired functions. For example, LCP 100 may communicate information, such as sensed electrical signals, data, instructions, messages, etc., to an external medical device through telemetry module 102. The external medical device may use the communicated signals, data, instructions and/or messages to perform various functions, such as determining occurrences of arrhythmias, delivering electrical stimulation therapy, storing received data, and/or performing any other suitable function. LCP 100 may additionally receive information such as signals, data, instructions and/or messages from the external medical device through telemetry module 102, and LCP 100 may use the received signals, data, instructions and/or messages to perform various functions, such as determining occurrences of arrhythmias, delivering electrical stimulation therapy, storing received data, and/or performing any other suitable function. Telemetry module 102 may be configured to use one or more methods for communicating with external devices. For example, telemetry module 102 may communicate via radiofrequency (RF) signals, inductive coupling, optical signals, acoustic signals, conducted communication signals, and/or any other signals suitable for communication.

In the example shown in FIG. 1, pulse generator module 104 may be electrically connected to electrodes 114. In some examples, LCP 100 may additionally include electrodes 114'. In such examples, pulse generator 104 may also be electrically connected to electrodes 114'. Pulse generator module 104 may be configured to generate electrical stimulation signals. For example, pulse generator module 104 may generate electrical stimulation signals by using energy stored in battery 112 within LCP 100 and deliver the generated electrical stimulation signals via electrodes 114 and/or 114'. Alternatively, or additionally, pulse generator 104 may include one or more capacitors, and pulse generator 104 may charge the one or more capacitors by drawing energy from battery 112. Pulse generator 104 may then use the energy of the one or more capacitors to deliver the generated electrical stimulation signals via electrodes 114 and/or 114'. In at least some examples, pulse generator 104 of LCP 100 may include switching circuitry to selectively connect one or more of electrodes 114 and/or 114' to pulse generator 104 in order to select which electrodes 114/114' (and/or other electrodes) pulse generator 104 delivers the electrical stimulation therapy. Pulse generator module 104 may generate electrical stimulation signals with particular features or in particular sequences in order to provide one or multiple of a number of different stimulation therapies. For example, pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy.

In some examples, LCP 100 may not include a pulse generator 104. For example, LCP 100 may be a diagnostic only device. In such examples, LCP 100 may not deliver electrical stimulation therapy to a patient. Rather, LCP 100 may collect data about cardiac electrical activity and/or physiological parameters of the patient and communicate such data and/or determinations to one or more other medical devices.

In some examples, LCP 100 may include an electrical sensing module 106, and in some cases, a mechanical sensing module 108. Electrical sensing module 106 may be configured to sense the cardiac electrical activity of the heart. For example, electrical sensing module 106 may be connected to electrodes 114/114', and electrical sensing module 106 may be configured to receive cardiac electrical signals conducted through electrodes 114/114'. The cardiac electrical signals may represent local information from the chamber in which LCP 100 is implanted. For instance, if LCP 100 is implanted within a ventricle of the heart, cardiac electrical signals sensed by LCP 100 through electrodes 114/114' may represent ventricular cardiac electrical signals. Mechanical sensing module 108 may include one or more sensors, such as an accelerometer, a blood pressure sensor, a heart sound sensor, a blood-oxygen sensor, and/or any other suitable sensors that are configured to measure one or more mechanical parameters of the patient. Both electrical sensing module 106 and mechanical sensing module 108 may be connected to a processing module 110, which may provide signals representative of the sensed mechanical parameters. Although described with respect to FIG. 1 as separate sensing modules, in some cases, electrical sensing module 206 and mechanical sensing module 208 may be combined into a single sensing module, as desired.

Electrodes 114/114' can be secured relative to housing 120 but exposed to the tissue and/or blood surrounding LCP 100. In some cases, electrodes 114 may be generally disposed on either end of LCP 100 and may be in electrical communication with one or more of modules 102, 104, 106, 108, and 110. Electrodes 114/114' may be supported by the housing 120, although in some examples, electrodes 114/114' may be connected to housing 120 only through short connecting wires such that electrodes 114/114' are not directly secured relative to housing 120. In examples where LCP 100 includes one or more electrodes 114', electrodes 114' may be generally disposed on the sides of LCP 100 and may increase the number of electrodes by which LCP 100 may sense cardiac electrical activity, deliver electrical stimulation and/or communicate with an external medical device. Electrodes 114/114' can be made up of one or more biocompatible conductive materials such as various metals or alloys that are known to be safe for implantation within a human body. In some instances, electrodes 114/114' connected to LCP 100 may have an insulative portion that electrically isolates electrodes 114/114' from adjacent electrodes, housing 120, and/or other parts of the LCP 100.

Processing module 110 can be configured to control the operation of LCP 100. For example, processing module 110 may be configured to receive electrical signals from electrical sensing module 106 and/or mechanical sensing module 108. Based on the received signals, processing module 110 may determine, for example, occurrences and, in some cases, types of arrhythmias. Based on any determined arrhythmias, processing module 110 may control pulse generator module 104 to generate electrical stimulation in accordance with one or more therapies to treat the determined arrhythmia(s). Processing module 110 may further receive information from telemetry module 102. In some examples, processing module 110 may use such received information to help determine whether an arrhythmia is occurring, determine a type of arrhythmia, and/or to take particular action in response to the information. Processing module 110 may additionally control telemetry module 102 to send information to other devices.

In some examples, processing module 110 may include a pre-programmed chip, such as a very-large-scale integration (VLSI) chip and/or an application specific integrated circuit (ASIC). In such embodiments, the chip may be pre-programmed with control logic in order to control the operation of LCP 100. By using a pre-programmed chip, processing module 110 may use less power than other programmable circuits (e.g. general purpose programmable microprocessors) while still being able to maintain basic functionality, thereby potentially increasing the battery life of LCP 100. In other examples, processing module 110 may include a programmable microprocessor. Such a programmable microprocessor may allow a user to modify the control logic of LCP 100 even after implantation, thereby allowing for greater flexibility of LCP 100 than when using a pre-programmed ASIC. In some examples, processing module 110 may further include a memory, and processing module 110 may store information on and read information from the memory. In other examples, LCP 100 may include a separate memory (not shown) that is in communication with processing module 110, such that processing module 110 may read and write information to and from the separate memory.

Battery 112 may provide power to the LCP 100 for its operations. In some examples, battery 112 may be a non-rechargeable lithium-based battery. In other examples, a non-rechargeable battery may be made from other suitable materials, as desired. Because LCP 100 is an implantable device, access to LCP 100 may be limited after implantation. Accordingly, it is desirable to have sufficient battery capacity to deliver therapy over a period of treatment such as days, weeks, months, years or even decades. In other examples, battery 110 may a rechargeable battery, which may help increase the useable lifespan of LCP 100. In still other examples, battery 110 may be some other type of power source, as desired.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. Anchor 116 may include any one of a number of fixation or anchoring mechanisms. For example, anchor 116 may include one or more pins, staples, threads, screws, helix, tines, and/or the like. In some examples, although not shown, anchor 116 may include threads on its external surface that may run along at least a partial length of anchor 116. The threads may provide friction between the cardiac tissue and the anchor to help fix the anchor 116 within the cardiac tissue. In other examples, anchor 116 may include other structures such as barbs, spikes, or the like to facilitate engagement with the surrounding cardiac tissue.

Figure 2:
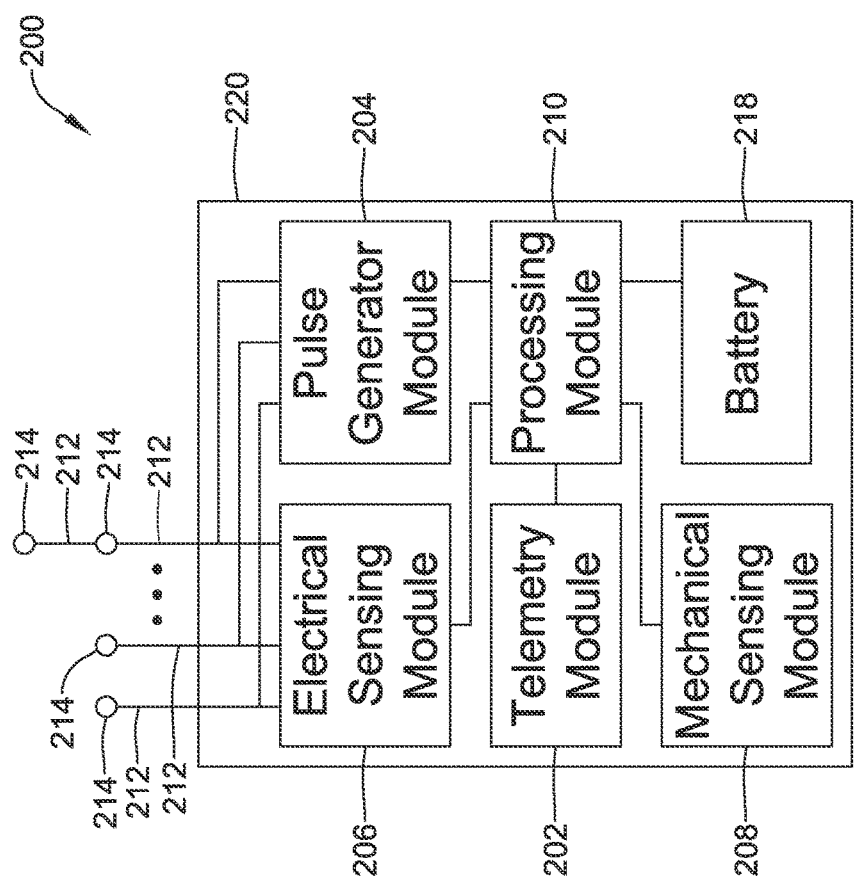
FIG. 2 is a schematic block diagram of another illustrative medical device that may be used in conjunction with the LCP of FIG. 1.

FIG. 2 depicts an example of another medical device (MD) 200, which may be used in conjunction with LCP 100 of FIG. 1 in order to detect and/or treat cardiac arrhythmias and other heart conditions. In the example shown, MD 200 may include a telemetry module 202, a pulse generator module 204, an electrical sensing module 206, a mechanical sensing module 208, a processing module 210, and a battery 218. Each of these modules may be similar to modules 102, 104, 106, 108, and 110 of LCP 100. Additionally, battery 218 may be similar to battery 112 of LCP 100. In some examples, however, MD 200 may have a larger volume within housing 220. In such examples, MD 200 may include a larger battery and/or a larger processing module 210 capable of handling more complex operations than processing module 110 of LCP 100.

While it is contemplated that MD 200 may be another leadless device such as shown in FIG. 1, in some instances MD 200 may include leads such as leads 212. Leads 212 may include electrical wires that conduct electrical signals between electrodes 214 and one or more modules located within housing 220. In some cases, leads 212 may be connected to and extend away from housing 220 of MD 200. In some examples, leads 212 are implanted on, within, or adjacent to a heart of a patient. Leads 212 may contain one or more electrodes 214 positioned at various locations on leads 212, and in some cases at various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously but adjacent the patient's heart. In some cases, electrodes 214 may conduct intrinsically generated electrical signals to leads 212, e.g. signals representative of intrinsic cardiac electrical activity. Leads 212 may, in turn, conduct the received electrical signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical signals and delivery the signals to the patient's heart (either directly or indirectly).

Mechanical sensing module 208, as with mechanical sensing module 108, may contain or be electrically connected to one or more sensors, such as accelerometers, blood pressure sensors, heart sound sensors, blood-oxygen sensors, and/or other sensors which are configured to measure one or more mechanical parameters of the heart and/or patient. In some examples, one or more of the sensors may be located on leads 212, but this is not required. In some examples, one or more of the sensors may be located in housing 220.

While not required, in some examples, MD 200 may be an implantable medical device. In such examples, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body.

In some cases, MD 200 may be an implantable cardiac pacemaker (ICP). In this example, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some examples, MD 200 may additionally be configured provide defibrillation therapy.

In some instances, MD 200 may be an implantable cardioverter-defibrillator (ICD). In such examples, MD 200 may include one or more leads implanted within a patient's heart. MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, MD 200 may be a subcutaneous implantable cardioverter-defibrillator (S-ICD). In examples where MD 200 is an S-ICD, one of leads 212 may be a subcutaneously implanted lead. In at least some examples where MD 200 is an S-ICD, MD 200 may include only a single lead which is implanted subcutaneously, but this is not required.

In some examples, MD 200 may not be an implantable medical device. Rather, MD 200 may be a device external to the patient's body, and may include skin-electrodes that are placed on a patient's body. In such examples, MD 200 may be able to sense surface electrical signals (e.g. cardiac electrical signals that are generated by the heart or electrical signals generated by a device implanted within a patient's body and conducted through the body to the skin). In such examples, MD 200 may be configured to deliver various types of electrical stimulation therapy, including, for example, defibrillation therapy.

Figure 3:
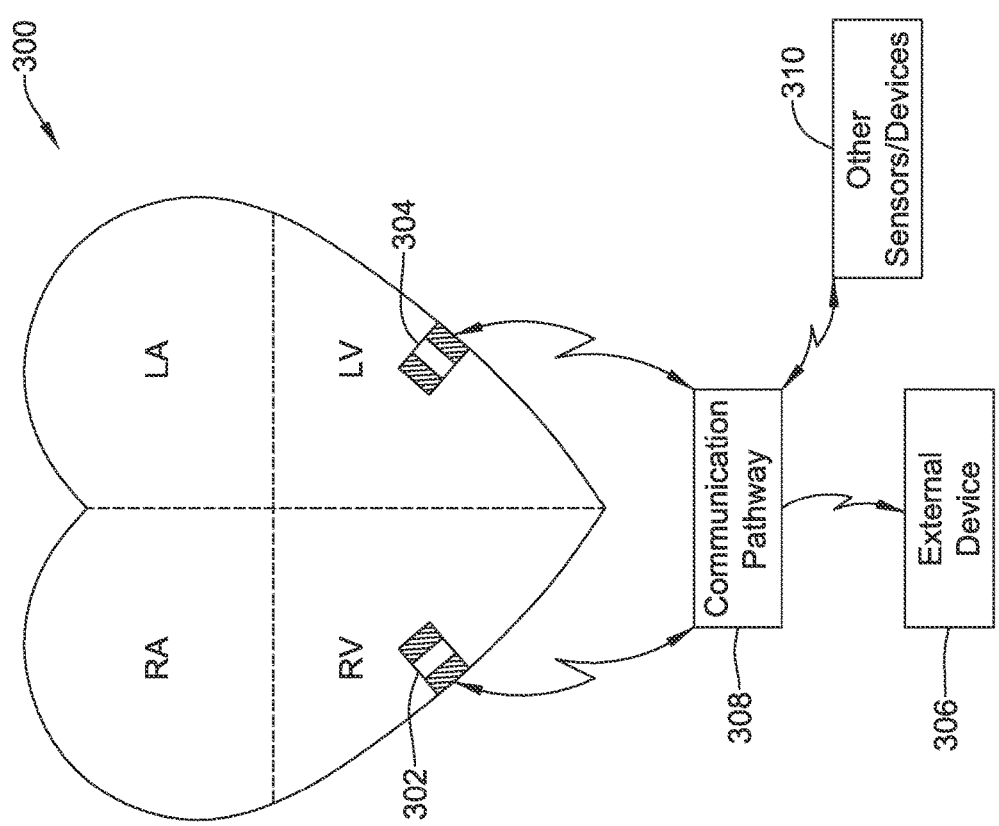
FIG. 3 is a schematic diagram of an exemplary medical system that includes multiple LCPs and/or other devices in communication with one another.

FIG. 3 illustrates an example of a medical device system and a communication pathway through which multiple medical devices 302, 304, 306, and/or 310 may communicate. In the example shown, medical device system 300 may include LCPs 302 and 304, external medical device 306, and other sensors/devices 310. External device 306 may be any of the devices described previously with respect to MD 200. Other sensors/devices 310 may also be any of the devices described previously with respect to MD 200. In some instances, other sensors/devices 310 may include a sensor, such as an accelerometer or blood pressure sensor, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one example, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. It is contemplated that communication pathway 308 may communicate using RF signals, inductive coupling, optical signals, acoustic signals, or any other signals suitable for communication. Additionally, in at least some examples, device communication pathway 308 may comprise multiple signal types. For instance, other sensors/device 310 may communicate with external device 306 using a first signal type (e.g. RF communication) but communicate with LCPs 302/304 using a second signal type (e.g. conducted communication). Further, in some examples, communication between devices may be limited. For instance, as described above, in some examples, LCPs 302/304 may communicate with external device 306 only through other sensors/devices 310, where LCPs 302/304 send signals to other sensors/devices 310, and other sensors/devices 310 relay the received signals to external device 306.

In some cases, communication pathway 308 may include conducted communication. Accordingly, devices of system 300 may have components that allow for such conducted communication. For instance, the devices of system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such examples, the delivered conducted communication signals (e.g. pulses) may differ from pacing or other therapy signals. For example, the devices of system 300 may deliver electrical communication pulses at an amplitude/pulse width that is sub-threshold to the heart.

Although, in some cases, the amplitude/pulse width of the delivered electrical communication pulses may be above the capture threshold of the heart, but may be delivered during a refractory period of the heart and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

Figure 4:
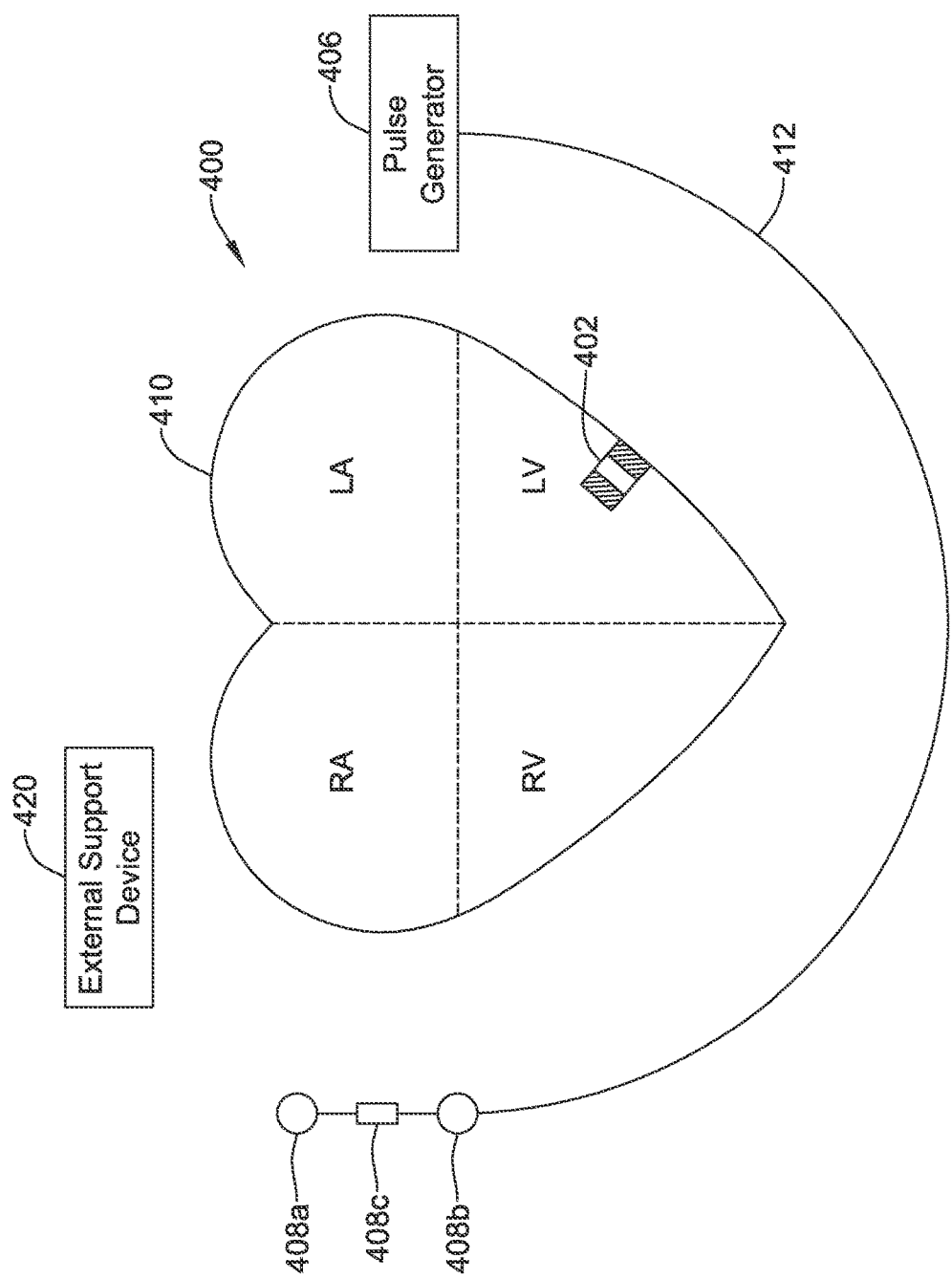
FIG. 4 is a schematic diagram of a system including an LCP and another medical device, in accordance with yet another example of the present disclosure.
Figure 5:
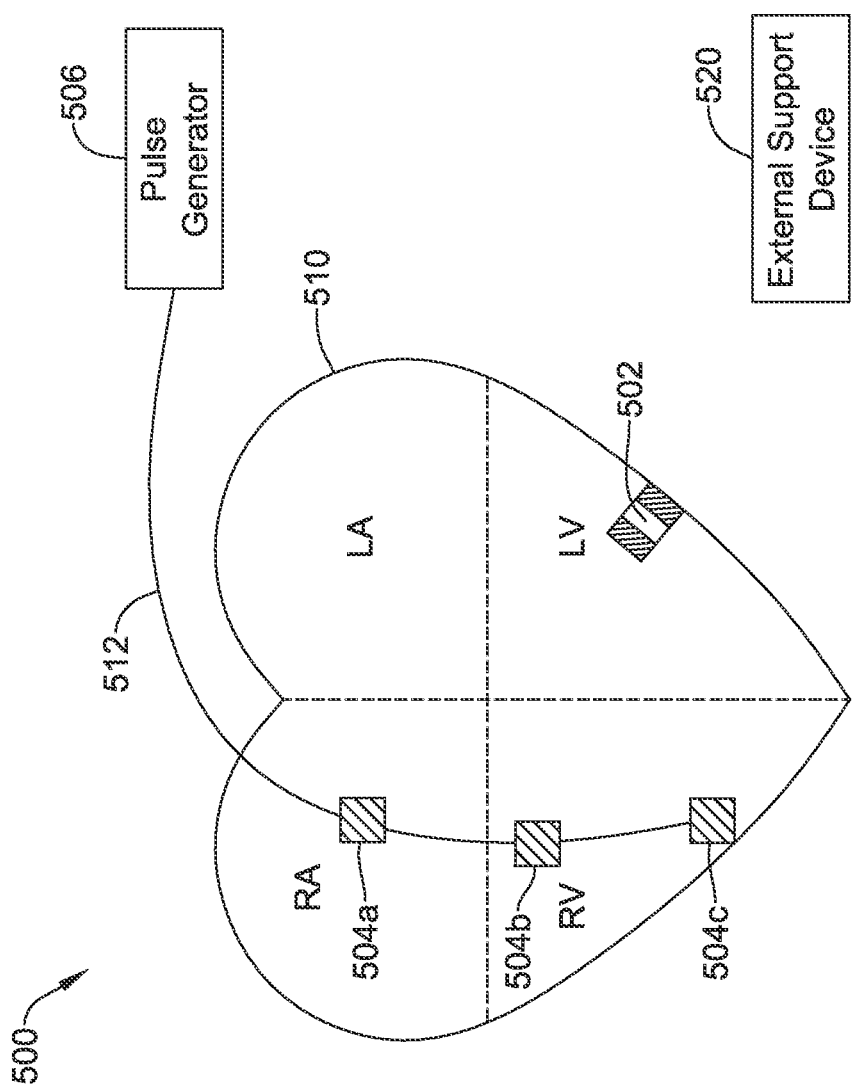
FIG. 5 is a schematic diagram of a system including an LCP and another medical device, in accordance with another example of the present disclosure.

FIGS. 4 and 5 show illustrative medical device systems that may be configured to operate according to techniques disclosed herein. In FIG. 4, an LCP 402 is shown fixed to the interior of the left ventricle of the heart 410, and a pulse generator 406 is shown coupled to a lead 412 having one or more electrodes 408a-408c. In some cases, the pulse generator 406 may be part of a subcutaneous implantable cardioverter-defibrillator (S-ICD), and the one or more electrodes 408a-408c may be positioned subcutaneously adjacent the heart. In some cases, the LCP 402 may communicate with the subcutaneous implantable cardioverter-defibrillator (S-ICD). In some cases, the LCP 302 may be in the right ventricle, right atrium or left atrium of the heart, as desired. In some cases, more than one LCP 302 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart.

In FIG. 5, an LCP 502 is shown fixed to the interior of the left ventricle of the heart 510, and a pulse generator 506 is shown coupled to a lead 512 having one or more electrodes 504a-504c. In some cases, the pulse generator 506 may be part of an implantable cardiac pacemaker (ICP) and/or an implantable cardioverter-defibrillator (ICD), and the one or more electrodes 504a-504c may be positioned in the heart 510. In some cases, the LCP 502 may communicate with the implantable cardiac pacemaker (ICP) and/or an implantable cardioverter-defibrillator (ICD).

The medical device systems 400 and 500 may also include an external support device, such as external support devices 420 and 520. External support devices 420 and 520 can be used to perform functions such as device identification, device programming and/or transfer of real-time and/or stored data between devices using one or more of the communication techniques described herein. As one example, communication between external support device 420 and the pulse generator 406 is performed via a wireless mode, and communication between the pulse generator 406 and LCP 402 is performed via a conducted mode. In some examples, communication between the LCP 402 and external support device 420 is accomplished by sending communication information through the pulse generator 406. However, in other examples, communication between the LCP 402 and external support device 420 may be via a telemetry module.

FIGS. 4-5 only illustrate two examples of medical device systems that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs without other devices such as pulse generator 406 or 506, with at least one LCP capable of delivering defibrillation therapy. In yet other examples, the configuration or placement of the medical devices, leads, and/or electrodes may be different from those depicted in FIGS. 4 and 5. Accordingly, it should be recognized that numerous other medical device systems, different from those depicted in FIGS. 4 and 5, may be operated in accordance with techniques disclosed herein. As such, the examples shown in FIGS. 4 and 5 should not be viewed as limiting in any way.

According to some examples, a medical device system of two or more medical devices may cooperate to deliver electrical stimulation therapy to a heart of a patient. For example, a plurality of medical devices may be configured to detect cardiac arrhythmias, determine whether the arrhythmias are susceptible to a first type of electrical stimulation therapy and if it is determined that the arrhythmia is not susceptible to the first type of electrical stimulation therapy or that the first type of electrical stimulation therapy has failed, to deliver a second type of electrical stimulation therapy. Many of the examples are described in terms tachyarrhythmias, anti-tachycardia pacing (ATP) therapy, and defibrillation shock therapy. However, other types of therapy are also contemplated, including cardiac resynchronization therapy (CRT), bradycardia therapy, neuro stimulation therapy, etc.

According to some techniques of this disclosure, both of a first device and a second device of a medical device system may determine an occurrence of a tachyarrhythmia, although this is not required. In some examples, the first device may determine the occurrence of a tachyarrhythmia based on sensed cardiac electrical signals, and may communicate the determination to the second device. In other examples, the second device may determine the occurrence of a tachyarrhythmia based on sensed cardiac electrical signals, and may communicate the determination to the first device. In yet other examples, the first device and the second device may both determine the occurrence of a tachyarrhythmia independently based on sensed cardiac electrical signals, and in still other examples, a device other than the first device and the second device may determine the occurrence of a tachyarrhythmia and may communicate the determination to the first device and/or the second device. Alternatively, one of the first and second devices may sense cardiac electrical signals, communicate those cardiac electrical signals to the other of the first and second devices, and the other of the first and second devices may use those received cardiac electrical signals to determine an occurrence of a tachyarrhythmia and may communicate that determination back to the first one of the first and second devices. The first and/or second devices may employ one or more techniques for determining occurrences of a tachyarrhythmia based on sensed cardiac electrical signals such as heart rate, a heart rhythm, ECG morphology, etc.

Additionally or alternatively, the first and/or second devices may determine occurrences of tachyarrhythmia based on one or more mechanical parameters of the patient, such as a heart contractility parameter, a heart sounds parameter, a cardiac output parameter, and/or a posture parameter. In some cases, the first and/or second devices may compare a heart contractility parameter to a contractility threshold. If the first and/or second devices determine that the heart contractility parameter is greater than (or, in some examples, less than) the contractility threshold, the first and/or second devices may determine an occurrence of a tachyarrhythmia. Additionally or alternatively, the first and/or second devices may compare a heart sounds parameter to a heart sounds threshold. If the first and/or second devices determine that the heart sounds parameter is greater than (or, in some examples, less than) the heart sounds threshold, the first and/or second devices may determine an occurrence of a tachyarrhythmia. Additionally or alternatively, the first and/or second devices may compare a cardiac output parameter to a cardiac output threshold. If the first and/or second devices determine that the cardiac output parameter is greater than (or, in some examples, less than) the cardiac output threshold, the first and/or second devices may determine an occurrence of a tachyarrhythmia. Additionally or alternatively, the first and/or second devices may compare a posture parameter to a posture threshold (e.g. a vertical posture parameter or a vertical posture threshold or a horizontal posture parameter to a horizontal posture parameter). If the first and/or second devices determine that the posture parameter is greater than (or, in some examples, less than) the posture threshold, the first and/or second devices may determine an occurrence of an arrhythmia.

Of course, the first and/or second devices may use a combination of the above described parameters in determining an occurrence of a tachyarrhythmia. For instance, the first and/or second devices may employ a hierarchical logic to determine an occurrence of a tachyarrhythmia. As one example, the first and/or second devices may use a first parameter to make an initial determination of an occurrence of a tachyarrhythmia, and may use a second parameter to confirm the initial determination before making a determination of an occurrence of a tachyarrhythmia. In other examples, the first and/or second devices may use additional parameters in making initial determinations or actual determinations. In other examples, the first and/or second devices may use a strict or weighted voting system using multiple of the parameters in making a determination of an occurrence of a tachyarrhythmia.

As one example, three of the parameters may indicate the occurrence of a tachyarrhythmia while two other parameters may not indicate an occurrence of a tachyarrhythmia. The first and/or second devices may then determine an occurrence of a tachyarrhythmia based on the greater number of parameters indicating an occurrence of a tachyarrhythmia. In other examples, the first and/or second devices may employ other, more complex, voting schemes to determine the occurrence of a tachyarrhythmia.

In some examples, the first and/or second devices may determine physiological parameters and/or occurrences of tachyarrhythmias based on information gathered by each device. For example, the first device may include one or more sensors that gather physiological parameters and/or an electrical sensing module that senses the cardiac electrical activity, and the first device may make one or more determinations based on the gathered information, such as determining whether a tachyarrhythmia is occurring. Alternatively, the first device may receive information, such as physiological parameters or sensed cardiac electrical activity from another device, for example the second device or another device of the system. In such examples, the first device may use the received information in determining physiological parameters and/or occurrences of, for example, tachyarrhythmias. In a similar manner, the second device may determine physiological parameters and/or occurrences of tachyarrhythmias based on information gathered by the second device or information received by the second device from other devices.

Figure 6:
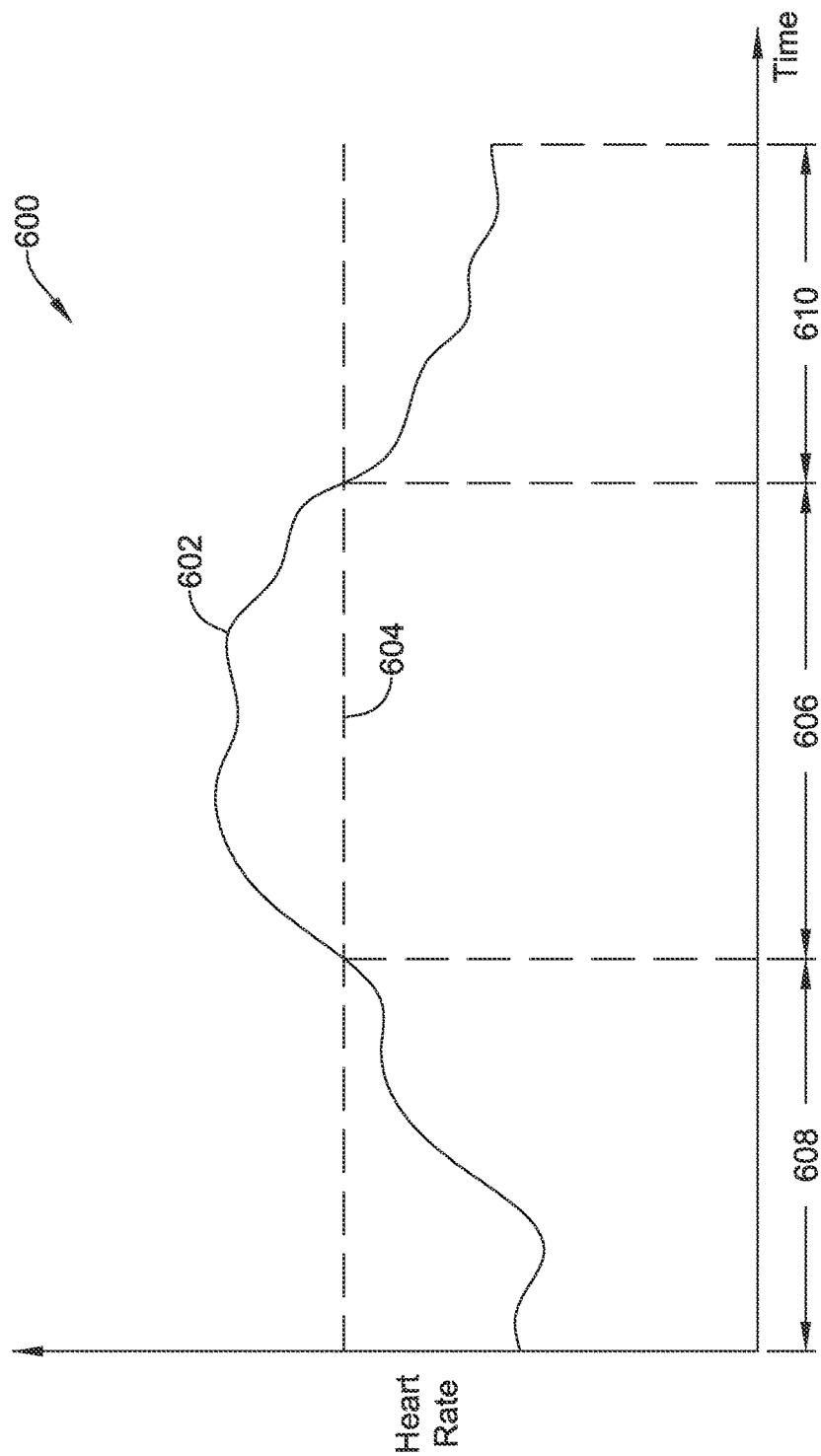
FIG. 6 is a graphical representation of an example heart rate including a heart rate threshold, in accordance with an example of the present disclosure.

FIG. 6 depicts example graph 600 of heart rate versus time including communication time periods 606, 608, and 610. FIG. 6 illustrates an example communication technique where a first medical device, such as LCP 100, only communicates the heart rate to a second medical device, such as MD 200, if the detected heart rate rises above a threshold, for example threshold 604. For instance, LCP 100 may monitor the heart rate by sensing one or more physiological parameters of a patient and determining a heart rate based on one or more of the sensed physiological parameters. Curve 602 may represent the heart rate determined by LCP 100 over time. While shown as a continuous curve, it is contemplated that the curve 602 may represent a series of discrete heart rates taken over time. Some example physiological parameters may include electrical signals (e.g. ECG), blood pressure, heart sounds, blood-oxygen levels, motion, and/or any other suitable physiological parameters. LCP 100 may determine the heart rate on a continuous, substantially continuous, periodic and/or on any other suitable basis.

In examples of FIG. 6, LCP 100 may be configured to only communicate the determined heart rate to MD 200 if the detected heart rate rises above threshold 604, such as during time period 606. Accordingly, LCP 100 may not communicate the determined heart rate to MD 200 during time periods 608 and 610. In some examples, when the heart rate is above threshold 604, LCP 100 may continuously or substantially continuously communicate the determined heart rate to MD 200. However, in other examples, LCP 100 may only periodically communicate the determined heart rate to MD 200 while the determined heart rate is above threshold 604. In such examples, LCP 100 may communicate the determined heart rate once every second, once every five seconds, or once every ten seconds, once every heart beat, once every 5 heart beats, or any other suitable period of time. When the heart rate falls back below threshold 604, LCP 100 may simply cease communicating the determined heart rate. In still other examples, LCP 100 may communicate an indication to MD 200 when the determined heart rate rises above threshold 604. In some instances, the indication may simply be an indication that the heart rate has risen above threshold 604, and in other instances the indication may comprise a value of the determined heart rate. In such examples, LCP 100 may additionally communicate an indication to MD 200 when the determined heart rate falls back below threshold 604. In some instances once the threshold 604 is crossed, MD 200 may communicate a new higher threshold to the LCP 100, and the process may be repeated.

LCP 100 may be programmed with the threshold 604 at implantation of LCP 100 or during a programming session. In other instances, threshold 604 may be programmed or updated at a different time. For example, LCP 100 may change the value of threshold 604 based on a value communicated to LCP 100 by MD 200 or another device. Additionally or alternatively, LCP 100 may adjust the value of threshold 604 based on one or more physiological parameters of the patient. For example, if a physiological parameter, such as blood pressure, increases above a predetermined value, or possibly decreases below a predetermined value, LCP 100 may adjust threshold 604 to a different value (e.g. to a greater or lower value by 10 beats/minute).

In at least some examples, LCP 100 may modify threshold 604 after communicating a determined heart rate to MD 200. For example, after receiving a determined heart rate or an indication that the determined heart rate has crossed the threshold 604, MD 200 may communicate another value for threshold 604 to LCP 100. LCP 100 may then adjust threshold 604 and begin comparing the determined heart rate to the new threshold 604. However, in other examples, LCP 100 may be preprogrammed with specific modifications to threshold 604 after the determined heart rate rises above threshold 604. In some cases, only after the determined heart rate rises above the new threshold 604 will the LCP 100 again communicate the determined heart rate or an indication that the determined heart rate has crossed the updated threshold 604 to the MD 200.

Figure 7:
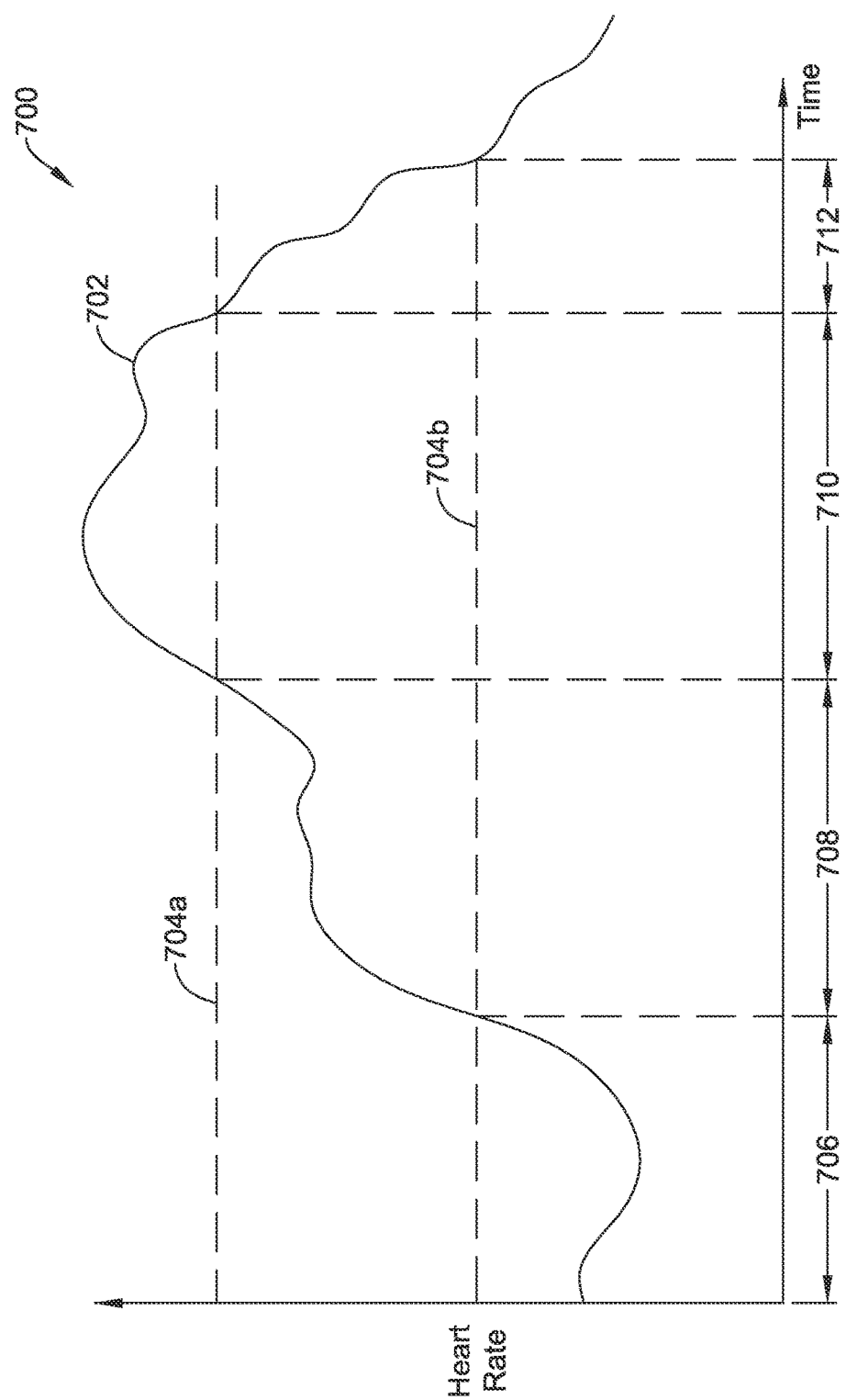
FIG. 7 is a graphical representation of an example heart rate including multiple heart rate thresholds, in accordance with an example of the present disclosure.

FIG. 7 depicts an example graph 700 of heart rate versus time including communication time periods 706, 708, 710, and 712. FIG. 7 illustrates example communication techniques that use multiple thresholds. As with the example described above with respect to FIG. 6, in the examples of FIG. 7, LCP 100 may monitor the heart rate by sensing one or more physiological parameters of a patient and determining a heart rate based on one or more of the sensed physiological parameters. Curve 702 may represent the heart rate determined by the LCP 100.

In some examples, LCP 100 may be configured to only communicate the determined heart rate to MD 200 after the heart rate rises above threshold 704a, such as during time period 710. Accordingly, LCP 100 may not communicate the determined heart rate to MD 200 during time periods 706, 708 and 712. When the heart rate is above threshold 704a, LCP 100 may continuously or substantially continuously communicate the determined heart rate to MD 200. However, in some instances, LCP 100 may only periodically communicate the determined heart rate to MD 200 while the determined heart rate is above threshold 704a. In such examples, LCP 100 may communicate the determined heart rate once every second, once every five seconds, once every ten seconds, once very heart beat, once every 5 heart beats, or any other suitable period of time. When the heart rate falls back below threshold 604, LCP 100 may simply cease communicating the determined heart rate. In still other examples, LCP 100 may communicate an indication to MD 200 when the determined heart rate rises above threshold 704a. In some instances, the indication may simply be an indication that the heart rate has risen above threshold 704a, and in other instances the indication may be the value of the determined heart rate. In such examples, LCP 100 may additionally communicate an indication to MD 200 when the determined heart rate falls back below threshold 704a.

In some examples, LCP 100 may be configured to communicate the determined heart rate to MD 200 if the heart rate rises above threshold 704b, such as during time periods 708, 710, and 712. Accordingly, LCP 100 may not communicate the determined heart rate to MD 200 during time period 706. When the heart rate is above threshold 704b, LCP 100 may continuously or substantially continuously communicate the determined heart rate to MD 200. However, in other examples, LCP 100 may only periodically communicate the determined heart rate to MD 200 while the determined heart rate is above threshold 704b. In such examples, LCP 100 may communicate the determined heart rate once every second, once every five seconds, or once every ten seconds, once very heart beat, once every 5 heart beats, or any other suitable period of time. When the heart rate falls back below threshold 704b, LCP 100 may simply cease communicating the determined heart rate. In still other examples, LCP 100 may communicate an indication to MD 200 when the determined heart rate rises above threshold 704b. In some instances, the indication may simply be an indication that the heart rate is above threshold 704b, and in other instances the indication may be the value of the determined heart rate. In such examples, LCP 100 may additionally communicate an indication to MD 200 when the determined heart rate falls back below threshold 704b.

In additional examples of FIG. 7, LCP 100 may be configured to communicate the determined heart rate to MD 200 when the heart rate rises above threshold 704b and when the heart rate rises above 704a. For example, LCP 100 may communicate a first indication to MD 200 when the determined heart rate rises above threshold 704b. In some instances, the first indication may be an indication that the heart rate is above threshold 704b, and in other instances the first indication may be the value of the determined heart rate. LCP 100 may additionally be configured to communicate second indication to MD 200 when the determined heart rate rises above threshold 704a. In some instances, the second indication may be an indication that the heart rate is above threshold 704a, and in other instances the second indication may be the value of the determined heart rate. LCP 100 may additionally be configured to communicate an indication to MD 200 when the determined heart rate falls below threshold 704a and when the threshold falls below threshold 704b.

In still other examples, LCP 100 may be configured to communicate the determined heart rate to MD 200 differently when the heart rate rises above threshold 704b and above 704a. For example, LCP 100 may not communicate the determined heart rate to MD 200 during time period 706. However, when the heart rate rises above threshold 704b, LCP 100 may communicate an indication to MD 200. In some instances, the indication may be an indication that the heart rate is above threshold 704b, and in other instances the indication may be the value of the determined heart rate. In some cases, the communication may include the value of threshold 704b (e.g. 100 beats/minute). LCP 100 may additionally communicate an indication to MD 200 when the determined heart rate falls below threshold 704b.

LCP 100 may be further configured to communicate an indication to MD 200 when the determined heart rate rises above threshold 704a. In some instances, the indication may be an indication that the heart rate is above threshold 704a, and in other instances the indication may be the value of the determined heart rate. In some cases, the communication may include the value of threshold 704a (e.g. 120 beats/minute). LCP 100 may additionally communicate an indication to MD 200 when the determined heart rate falls below threshold 704a.

As with the examples of FIG. 6, in the examples of FIG. 7, LCP 100 may be programmed with thresholds 704a and 704b at implantation of LCP 100 or during a programming session. In some examples, thresholds 704a and 704b may be programmed or updated at other times. For example, LCP 100 may change the value of threshold 704a and/or 704b based on values for thresholds 704a/704b communicated to LCP 100 by MD 200 or another device. Additionally or alternatively, LCP 100 may adjust the value of thresholds 704a/704b based on one or more physiological parameters of the patient. For example, if a physiological parameter, such as blood pressure, increases above a predetermined value, or possibly decreases below a predetermined value, LCP 100 may adjust threshold 604 to a different value (e.g. to a greater or lower value by, for example, 10 beats/minute). In still other examples, threshold 704a/704b may be communicated to LCP 100 my MD 200 or another medical device. In some of these examples, MD 200 or another medical device may only initially communicate threshold 704b and may later communicate threshold 704a after receiving an indication that the determined heart rate rose above threshold 704b.

In examples where LCP 100 is only initially be programmed with threshold 704*a*, LCP 100 may operate according to one or more of the techniques described with respect to FIG. 6 for a single threshold. LCP 100 may then receive a second threshold value, for example a threshold relating to 704*b*. In such examples, LCP 100 may transition to one of the techniques described with respect to FIG. 7 including multiple thresholds. For example, before receiving a value for a second threshold, LCP 100 may be configured to communicate the determined heart rate continuously, substantially continuously, periodically, or once, when the heart rate rises above a first threshold, such as threshold 704*b*. After receiving a value for a second threshold, such as 704*a*, from another medical device, LCP 100 may transition to one of the techniques described above including multiple thresholds. For example, LCP 100 may cease communicating the determined heart rate on the continuous, substantially continuous, or periodic basis even though the heart rate is still above threshold 704*b*. However, once the heart rate rises above threshold 704*a*, LCP 100 may communicate the determined heart rate, sometimes continuously, substantially continuously, periodically, or once, as described in previous examples.

Figure 8:
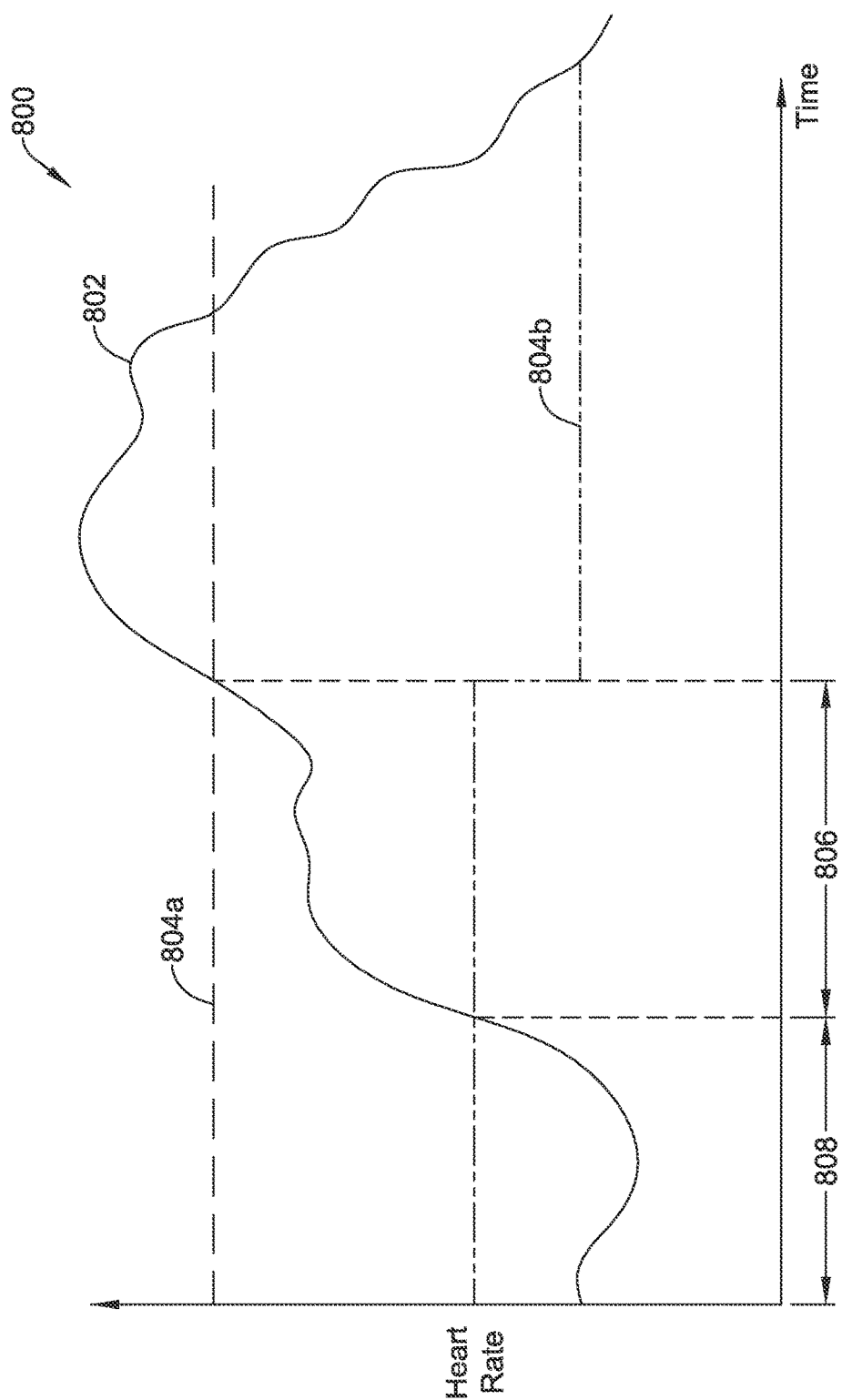
FIG. 8 is a graphical representation of an example heart rate including multiple heart rate thresholds, in accordance with an example of the present disclosure.

FIG. 8 depicts example graph 800 of heart rate versus time. FIG. 8 illustrates an example communication technique including multiple thresholds. As with the examples described with respect to FIGS. 6-7, in the examples of FIG. 8, LCP 100 may monitor the heart rate by sensing one or more physiological parameters of a patient and determining a heart rate based on one or more of the sensed physiological parameters. Curve 802 may represent the heart rate determined by LCP 100. In some examples of FIG. 8, LCP 100 may be configured to operate according to any of the techniques described above with respect to FIGS. 6-7. However, LCP 100 may be further configured to modify one of the thresholds after the determined heart rate rises above a threshold. For example, LCP 100 may be configured to communicate an indication to MD 200 when the determined heart rate rises above threshold 804*b*, such as at time 808. LCP 100 may additionally be configured to communicate the determined heart rate to MD 200 continuously, substantially continuously, periodically, or once, after the determined heart rate rises above threshold 804*a*. In some instances, LCP 100 may additionally be configured to modify threshold 804*b* once the determined heart rate rises above threshold 804*a*. As shown in FIG. 8, this modification may be to decrease threshold 804*b* by a predetermined amount. In other examples, the modification may be to increase threshold 804*b*. Alternatively, the decreased or increased threshold 804*b* may simply be an alternate threshold that is higher or lower than threshold 804*b* by the predetermined amount. Once the determined heart rate falls below threshold 804*b*, LCP 100 may then adjust threshold 804*b* back to its original value. This may introduce a level of hysteresis into the system.

In some examples of FIG. 8, LCP 100 may modify threshold 804*a* in a manner pre-programmed into LCP 100. However, in other examples, MD 200 may communicate to LCP 10 how to modify the threshold. For example, MD 200 may communicate such a modification after receiving a communication from LCP 100 indicating that the heart rate has risen above threshold 804*a*.

Figure 9:
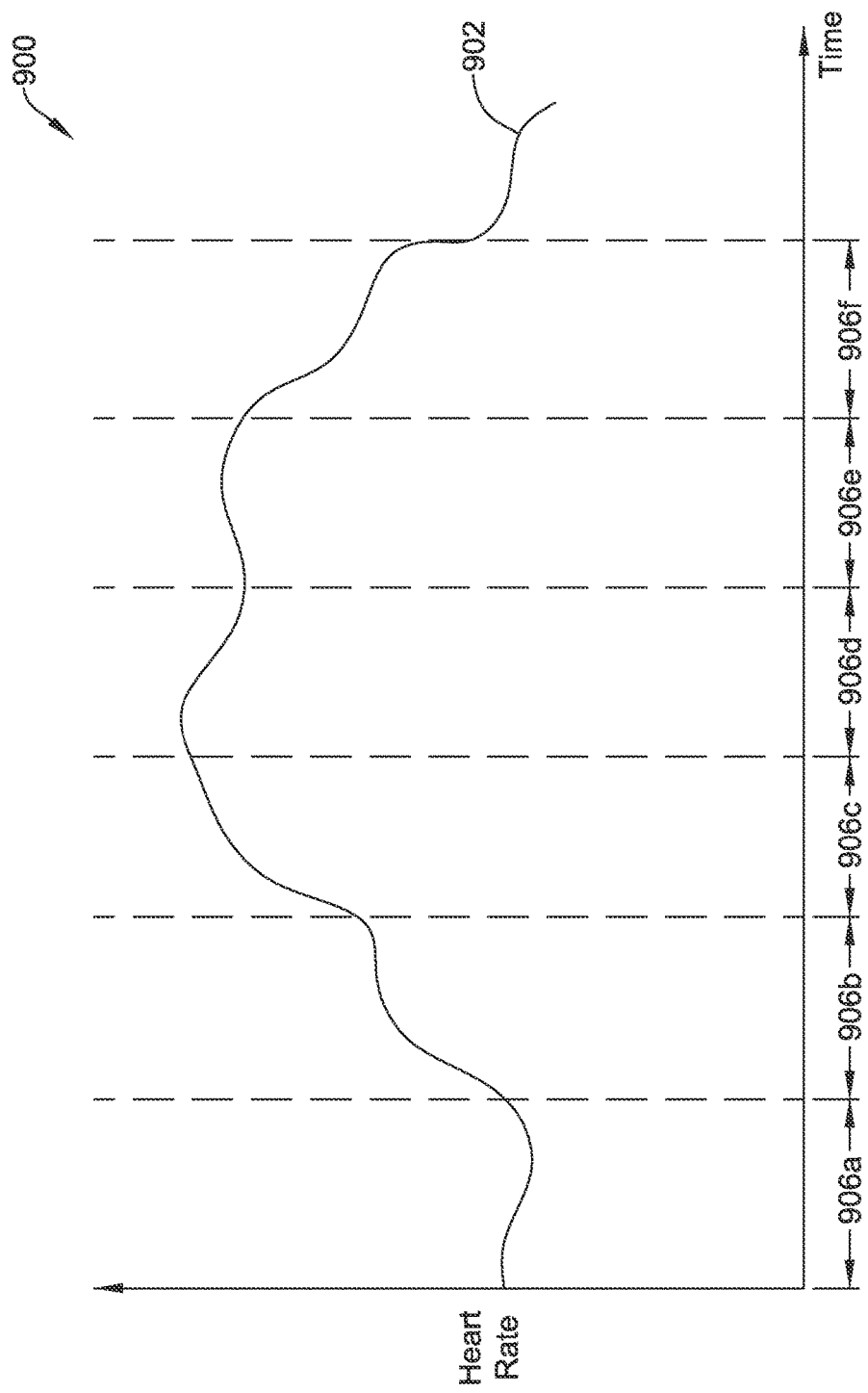
FIG. 9 is a graphical representation of an example heart rate including multiple heart rate detection regions, in accordance with an example of the present disclosure.

FIG. 9 depicts an example graph 900 of heart rate versus time. FIG. 9 illustrates an example communication technique including multiple time periods 906*a-f*. As with the examples described with respect to FIGS. 6-8, in the examples of FIG. 9, LCP 100 may monitor the heart rate by sensing one or more physiological parameters of a patient and determining a heart rate based on one or more of the sensed physiological parameters. Curve 902 may represent the heart rate determined by LCP 100.

In some examples of FIG. 9, instead of employing absolute thresholds, LCP 100 may determine whether to communicate the determined heart rate to MD 200 based on relative changes to the determined heart rate. For example, LCP 100 may, for a period of time, record the determined heart rate and determine an average baseline heart rate for that time period. Alternatively, and in another example, LCP 100 may, for a period of time, record a maximum, a minimum, or a mean value of the determined heart rate and determine a baseline heart rate for that time period. LCP 100 may then compare a current determined heart rate to the determined baseline heart rate. If the current determined heart rate rises above the determined baseline heart rate by a first predetermined amount, LCP 100 may communicate the determined heart rate to MD 200. In some examples, the first predetermined amount may be a specific absolute value (e.g. 10 beats/minute). In other examples, the first predetermined amount may be a changing variable, for example a percentage of the determined baseline value.

Accordingly, in the context of FIG. 9, LCP 100 may monitor the heart rate during time period 906*a*. At the end of time period 906*a*, LCP 100 may determine a baseline heart rate for time period 906*a*. Then, during time period 906*b*, LCP 100 may compare the current determined heart rate to the determined baseline heart rate for time period 906*a* plus the first predetermined amount. If the current determined heart rate is above the determined baseline heart rate plus the first predetermined amount for time period 906*a*, LCP 100 may communicate the determined heart rate to MD 200. At the end of time period 906*b*, LCP 100 may compare the current determined heart rates in time period 906*c* to the determined baseline heart rate for time period 906*a* plus the first predetermined amount. This process may continue on for time periods 906*d*-906*f*.

In some cases, the LCP 100 may update the determined baseline heart rate. For example, the LCP 100 may update the determined baseline heart rate by determining a baseline heart rate for time period 906*b*, and then compare the current determined heart rate during time period 906*c* to the determined baseline heart rate for time period 906*b* plus the first predetermined amount. In other cases, the LCP 100 may update the determined baseline heart rate after the current determined heart rate exceeds the determined baseline heart rate plus the first predetermined amount and the LCP 100 has communicated the determined heart rate to MD 200.

When LCP 100 communicates the determined heart rate to MD 200, LCP 100 may continuously or substantially continuously communicate the determined heart rate to MD 200. However, in other examples, LCP 100 may only periodically communicate the determined heart rate to MD 200. In such examples, LCP 100 may communicate the determined heart rate once every second, once every five seconds, or once every ten seconds, once every heat beat, once every 5 heart beats, or any other suitable period of time. In still other examples, LCP 100 may communicate an indication to MD 200. In some instances, the indication may simply be an indication that the determined heart rate has crossed the determined baseline heart rate plus the first predetermined amount, and in other instances the indication may include the value of the determined heart rate.

After determining that a current determined heart rate exceeds a previously determined baseline heart rate plus the first predetermined amount and communicating the determined heart rate to MD 200, LCP 100 may compare the current determined heart rate to the previously determined baseline heart rate less a second predetermined amount. As with the first predetermined amount, in some examples, the second predetermined amount may be a specific absolute value. In other examples, the second predetermined amount may be a changing variable, for example a percentage of the determined baseline heart rate value. Additionally, the second predetermined amount may be different from the first predetermined amount. For example, the second predetermined amount may be less than the first predetermined amount.

After a first determination that a current determined heart rate exceeds a previously determined baseline heart rate plus the first predetermined amount, LCP 100 may maintain that determined baseline heart rate as the baseline heart rate for future comparisons. As an illustrative example, in FIG. 9, LCP 100 may determine for the first time that a current determined heart rate exceeds a determined baseline heart rate plus the first predetermined amount during time period 906c. Accordingly, the determined baseline heart rate that LCP 100 compares the current determined heart rate to (plus the first predetermined amount) is the baseline heart rate during time period 906b. Subsequently, LCP 100 may maintain the baseline heart rate of time period 906b as the baseline heart rate for comparison with future current determined heart rates. Although, in other examples, LCP 100 may continually determine new baseline heart rates, as appropriate, and compare the current determined heart rate to the new baseline heart rates. After determining that a current determined heart rate is less than the previously determined baseline heart rate (and in some cases less the second predetermined amount), LCP 100 may either cease communicating the heart rate to MD 200 or communicate another indication to MD 200 indicating the fall of the heart rate below the previously determined baseline heart rate (sometimes less the second predetermined amount), as appropriate.

In some examples, LCP 100 may adjust the first predetermined amount based on the value of the determined baseline heart rate. For instance, in the example of FIG. 9, the determined baseline rate for time period 906a may be one hundred beats per minute. Additionally, LCP 100 may determine the first predetermined amount to be thirty beats per minute. Accordingly, if during time period 906b LCP 100 determines that the heart rate rises above one hundred thirty beats, LCP 100 may then communicate the heart rate to MD 200. In example where LCP 100 determine different baseline heart rates for different time periods, LCP 100 may determine a baseline heart rate for time period 906b of one hundred twenty beats per minute (possibly based on determined heart rates during time period 906a). Accordingly, LCP 100 may then determine a first predetermined time period of twenty beats per minute. This means that during time period 906b, LCP 100 may communicate the determined heart rate to MD 200 if the determined heart rate exceeds one hundred forty beats per minute. As another example, LCP 100 may then determine a baseline heart rate for time period 906c of one hundred forty-five beats per minute (possibly based on determined heart rates during time period 906b). LCP 100 may then determine the first predetermined amount to be ten beats per minute. Accordingly, LCP 100 may communicate the determined heart rate to MD 200 if the determined heart rate exceeds one hundred fifty-five beats per minute.

In some instances, LCP 100 may communicate the current determined heart rate to MD 200 without LCP 100 using thresholds or determining a baseline heart rate. For instance, in some examples, LCP 100 may only communicate the determined heart rate to MD 200 based on a request sent from MD 200. In such examples, MD 200 may independently determine a heart rate and may use the MD 200 determined heart rate to determine occurrences of, for example, arrhythmias. When MD 200 determines an occurrence of an arrhythmia, or in some examples a heart rate exceeding a threshold but not necessarily indicative of an arrhythmia, MD 200 may send a request to LCP 100 to communicate the determined heart rate (e.g. the heart rate determined by LCP 100 based on signals sensed by LCP 100). The communication by MD 200 may trigger LCP 100 to communicate a single determined heart rate or to begin a communication stream of determined heart rates (e.g. continuously, substantially continuously, or periodically). MD 200 may receive such a communication or communications and then attempt to confirm the determined occurrence of the arrhythmia by determining whether an arrhythmia is occurring based on the communicated heart rate from LCP 100. After MD 200 determines no occurrence of an arrhythmia (for example MD 200 falsely determined an occurrence of an arrhythmia or after termination of a true arrhythmia), or that the communicated heart rate fell below a threshold, MD 200 may send another communication to LCP 100 to cease communicating the determined heart rate to MD 200. Alternatively, after determining an occurrence of an arrhythmia, or simply determining a heart rate above a threshold, MD 200 may send a communication to LCP 100 to begin to communicate the heart rate determined by LCP 100 based on any of the above described techniques with respect to FIGS. 6-9 to MD 200.

In additional examples, any of the examples described herein may further employ multiple thresholds related to different determined parameters. As one example, a first parameter may be heart rate. In such examples, LCP 100 may operate according to any of the above described techniques and compare a determined heart rate to a first heart rate threshold. Once LCP 100 has determined that the heart rate exceeds the first heart rate threshold, LCP 100 may communicate the determined heart rate or an indication to another medical device, in accordance with any of the examples described herein. However, instead of comparing the determined heart rate to a second heart rate threshold, LCP 100 may compare a different parameter, for instance QRS width, to a different threshold, such as a QRS width threshold. In this manner, LCP 100 may employ a hierarchy of parameter thresholds whereby LCP 100 actively compares various parameters to associated thresholds at different times according to a logic scheme, thereby saving stored battery energy. Of course, in other examples, instead of ceasing to compare the heart rate to a heart rate threshold after determining that the heart rate exceeds a first heart rate threshold, LCP 100 may compare the heart rate to a second heart rate threshold in addition to comparing the QRS width to a QRS width threshold. In such examples, comparing multiple parameters to multiple thresholds may provide more robust information about a condition of the heart of the patient. Additionally, such techniques are not specific to any particular parameters. The first parameter, heart rate in the above examples, and the second parameter, QRS width in the above examples, may be any of the parameters indicated herein. Further, such a logic scheme may employ multiple first parameters, multiple second parameters, or even third or more parameters if one or more of the first and/or second parameters rise above a threshold.

In some cases, and for all of the examples discussed herein, rather than comparing a single current determined heart rate, it is contemplated that the LCP 100 may, for a period of time, determine an average heart rate for a time period and then compare the determined average heart rate for that period of time to the baseline heart rate (e.g. wherein the baseline heart rate is established during a previous period of time). Alternatively, the LCP 100 may, for a period of time, record a maximum, a minimum, or a mean value of the determined heart rate for that time period and then compare that determined heart rate for that period of time to the baseline heart rate (e.g. wherein the baseline heart rate is established during a previous period of time). These are just some examples. Such an implementation may help filter out some of the noise from the determined heart rate before making the comparison.

Alternatively, in any of the examples described herein, instead of a device communicating a threshold to another device, the communicating device may communicate a delta value. The delta value may be a value by which the receiving medical device should adjust the current threshold. For example, if the received delta value is a positive ten beats/minute, the receiving device may add ten beats/minute to the current threshold, thereby creating a second threshold. In some instances, the delta value may be negative, thereby indicating that the receiving device should decrease the threshold by the received delta value.

As previously noted, the above described techniques should not be construed as being limited to only communications about heart rates. The above described techniques are applicable to any parameter monitored by at least a first device and communicated to another device. For instance, some example patient physiological parameters may include QRS width, long V-A, A-V, or V-V intervals (in systems where one device has access to multi-chamber information), T-wave amplitude, activity amplitude (e.g. from an accelerometer), posture, and/or any other suitable physiological parameter. In one example, the first medical device, e.g. LCP 100, may monitor any of these physiological parameters and communicate them to another medical device, e.g. MD 200, in accordance with any of the above described techniques.

These techniques may be equally applicable to device parameters such as an error threshold. For instance, LCP 100 may have an error flag value stored internally, which may have a value of zero when LCP 100 has no error conditions. When LCP 100 detects an error condition, LCP 100 may set the error flag to a value of one. Example error conditions may relate to memory of the device or other hardware components. LCP 100 may compare the value of the error flag to an error flag threshold, such as one-half and when LCP 100 determines that value of the error flag is greater than the error flag threshold, LCP 100 may communicate the error condition to another medical device, such as MD 200, in accordance with any of the communicate techniques described herein. When the value of the error flag is less than the error flag threshold, LCP 100 may not communicate any error condition to any other medical device.

Additionally, the techniques described herein may be equally applicable to various device parameters and other parameters. For instance, LCP 100 may monitor device parameters such as a battery voltage parameter, a clock frequency or speed parameter, a lead impedance parameter, a current parameter, and/or other device parameters. LCP may also monitor other parameters such as flags for if therapy has been delivered. LCP 100 may monitor such device or other parameters and compare the parameters to associated thresholds, in accordance with any of the above described techniques. Additionally, LCP 100 may not communicate values of the parameters when the values of the parameters are below their associated threshold(s). LCP 100 may then communicate values of the parameter(s) or indication(s) to another medical device when LCP 100 determines that the determined value(s) of one or more of the parameters exceeds the associated threshold(s). LCP 100 may communicate such values or indications in accordance with any of the techniques described herein.

LCP 100 may further implement a technique for ensuring that another medical device has actually received communications from LCP 100 in any of the above described techniques. For example, as described herein after determining that a parameter has exceeded a threshold, LCP 100 may communicate a value of the parameter or an indication that the value of the parameter has exceeded its associated threshold. Once LCP 100 has sent a communication, another medical device may receive the communication. The other medical device may then send an acknowledgement to LCP 100. LCP 100 may wait a predetermined amount of time to receive such an acknowledgement from the other medical device, wherein the acknowledgement indicates that the other medical device has received the communication from LCP 100. In some examples, the predetermined amount of time may be, for example, two hundred fifty milliseconds, five hundred milliseconds, seven hundred fifty milliseconds, or one second or any other suitable length of time. If, during the predetermined amount of time, LCP 100 does not receive an acknowledgement from the other medical device, LCP 100 may communicate the value of the parameter or an indication that the value of the parameter rose above the associated threshold again, and may again wait a predetermined period of time.

Figure 10:
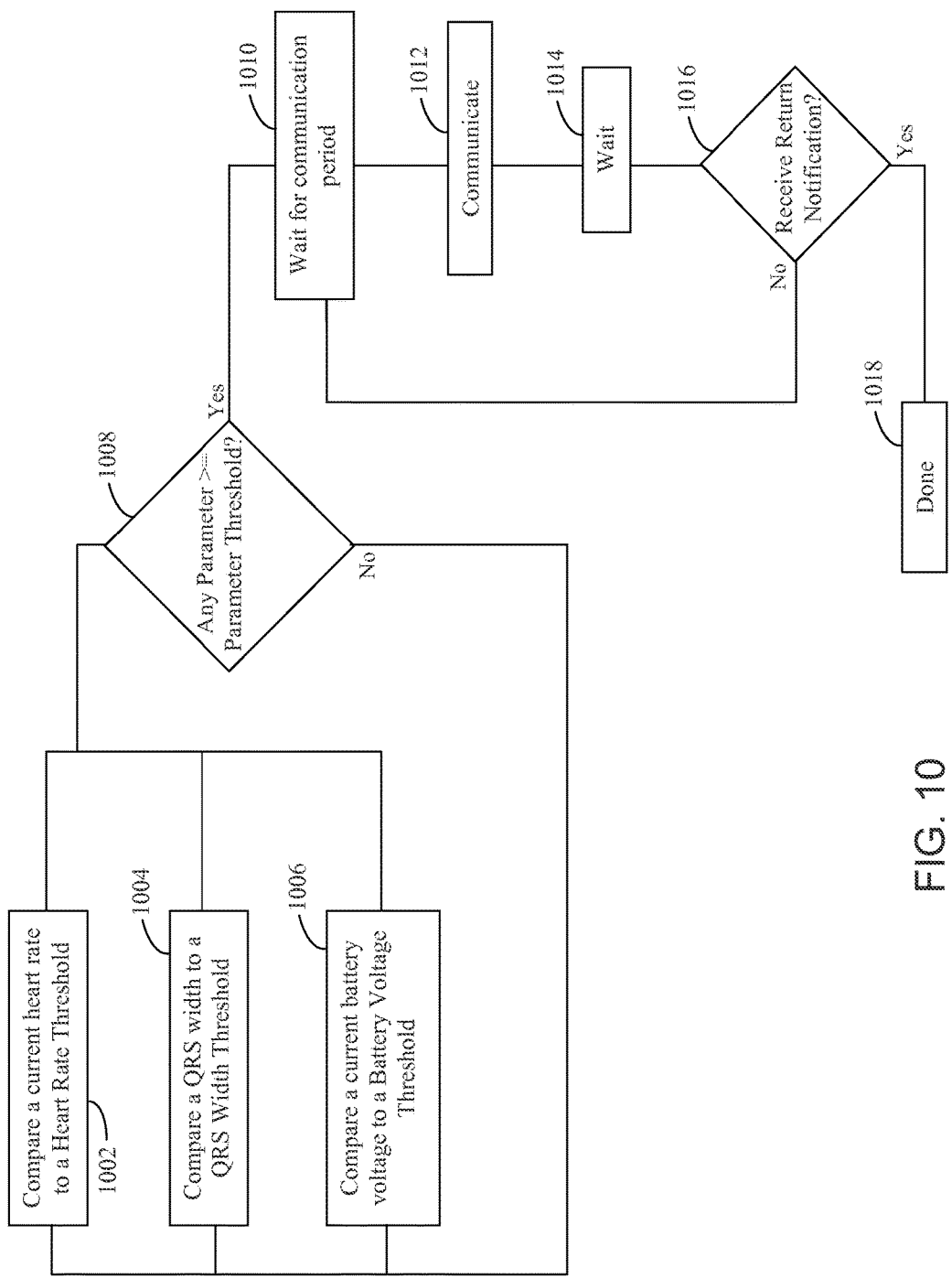
FIG. 10 is a flow diagram of an illustrative method that may be implemented by a medical device or medical device system, such as the illustrative medical devices and medical device systems described with respect to FIGS. 1-4.

Additionally, LCP 100 may monitor multiple parameters simultaneously. FIG. 10 illustrates a flow diagram of one example technique for monitoring various parameters simultaneously. LCP 100 may determine and monitor heart rate, QRS width, and battery voltage parameters. LCP 100 may additionally compare a determined current heart rate to a heart rate threshold, as shown at 1002, a determined QRS width to a QRS width threshold, as shown at 1004, and a determined current battery voltage to a battery voltage threshold, as shown at 1006. LCP 100 may further determine whether any of the determined heart rate, QRS width, and battery voltage parameters are equal to or above their associated thresholds, as shown at 1008. If LCP 100 determines that none of the heart rate, QRS width, and battery voltage parameters are equal to or above their associated thresholds, LCP 100 may continue to compare the determined current heart rate to the heart rate threshold, the determined QRS width to the QRS width threshold, and the determined current battery voltage to the battery voltage threshold, as shown by the "no" branch of 1008.

If LCP 100 determines that any of the heart rate, QRS width, and battery voltage parameters are equal to or greater than their associated thresholds, indicated by the "yes" branch of 1008, LCP 100 may then wait for a communicated period, as shown at 1010. For example, LCP 100 may have one or more defined communicate time periods, possibly indicated in a communication protocol implemented by LCP 100. Once LCP 100 determines a communication period in which LCP 100 may communicate, LCP 100 then communicates a value of the parameter whose value was equal to or greater than its associated threshold, or an indication that the value of the parameter is equal to or greater than its associated threshold, to another medical device as indicated at 1012. LCP 100 may communicate the value or indication in accordance with any of the techniques described herein (e.g. continuously, substantially continuously, periodically, or once).

After communicating the value of an indication, LCP 100 may wait a predetermined amount of time, as indicated at 1014. The predetermined period may be, for example, two hundred fifty milliseconds, five hundred milliseconds, seven hundred fifty milliseconds, or one second or any other suitable length of time. During this predetermined amount of time, any receiving medical device may communicate a confirmation notification to LCP 100. Accordingly, either throughout the predetermined amount of time or at the end of the predetermined amount of time, LCP 100 may determine whether it has received such a confirmation communication, as shown at 1016. If LCP 100 has not received a confirmation notification, LCP 100 may again attempt to communicate the value or indication, as indicated by the "no" branch of 1016. If LCP 100 has received a confirmation notification, as indicated by the "yes" branch of 1016, LCP 100 may end the method, as indicated at 1018. LCP 100 may then adjust the threshold of the parameter that was equal to or greater than its associated threshold in accordance with any of the techniques disclosed herein.

As another note, although the examples described herein used examples where a parameter rising above a threshold triggers another step, an action, or some other function, the scope of this disclosure should not be considered limited to this description. For instance, other examples within the scope of this disclosure include monitoring for when parameters fall below a threshold. Just as it may be dangerous for a heart rate to rise above a threshold, it may also be dangerous for a heart rate to fall below a threshold. This may be true for many of the other parameters disclosed herein as well. Accordingly, this disclosure should be viewed as encompassing examples whereby monitoring for when a parameter falls below a threshold may be interchanged in any of the above examples with a parameter being monitored for when the parameter rises above a threshold.

Figure 11:
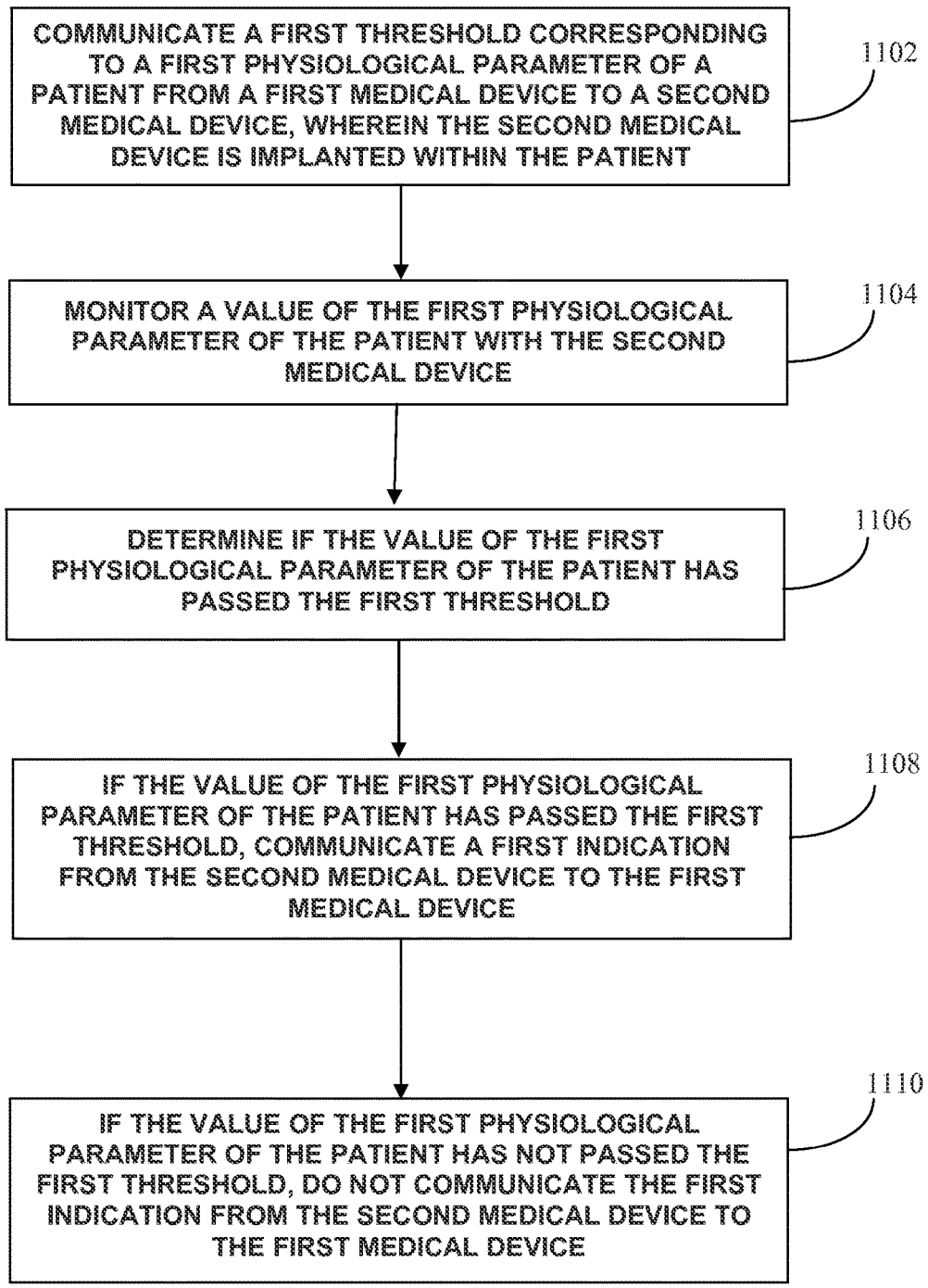
FIG. 11 is a flow diagram of an illustrative method that may be implemented by a medical device or medical device system, such as the illustrative medical devices and medical device systems described with respect to FIGS. 1-4.

FIG. 11 is a flow diagram of an illustrative method that may be implemented by an implantable medical device, such as shown in FIGS. 1 and 2, or a medical device system such as shown in FIGS. 3 and 4. Although the method of FIG. 11 will be described with respect to LCP 100, the illustrative method of FIG. 11 may be performed using any suitable medical device or medical device system.

According to the method depicted in FIG. 11, a first medical device may be implanted within a patient, such as if the first medical device is an ICP, an ICD, an S-ICD, or may be disposed in proximity to the patient, such as if the first medical device is an external medical device. The first medical device may be part of a medical device system along with a second medical device, such as LCP 100. In such a medical device system, the first medical device may communicate a first threshold corresponding to a first physiological parameter of a patient to LCP 100, wherein LCP 100 is implanted within the patient, as shown at 1102. Additionally, LCP 100 may monitor a value of the first physiological parameter of the patient, as shown at 1104. LCP 100 may further determine if the value of the first physiological parameter of the patient has passed the first threshold, as shown at 1106. If the value of the first physiological parameter of the patient has passed the first threshold, LCP 100 may communicate a first indication to the first medical device, as shown at 1108. Finally, if the value of the first physiological parameter of the patient has not passed the first threshold, LCP 100 may not communicate the first indication to the first medical device, as shown at 1110.

Figure 12:
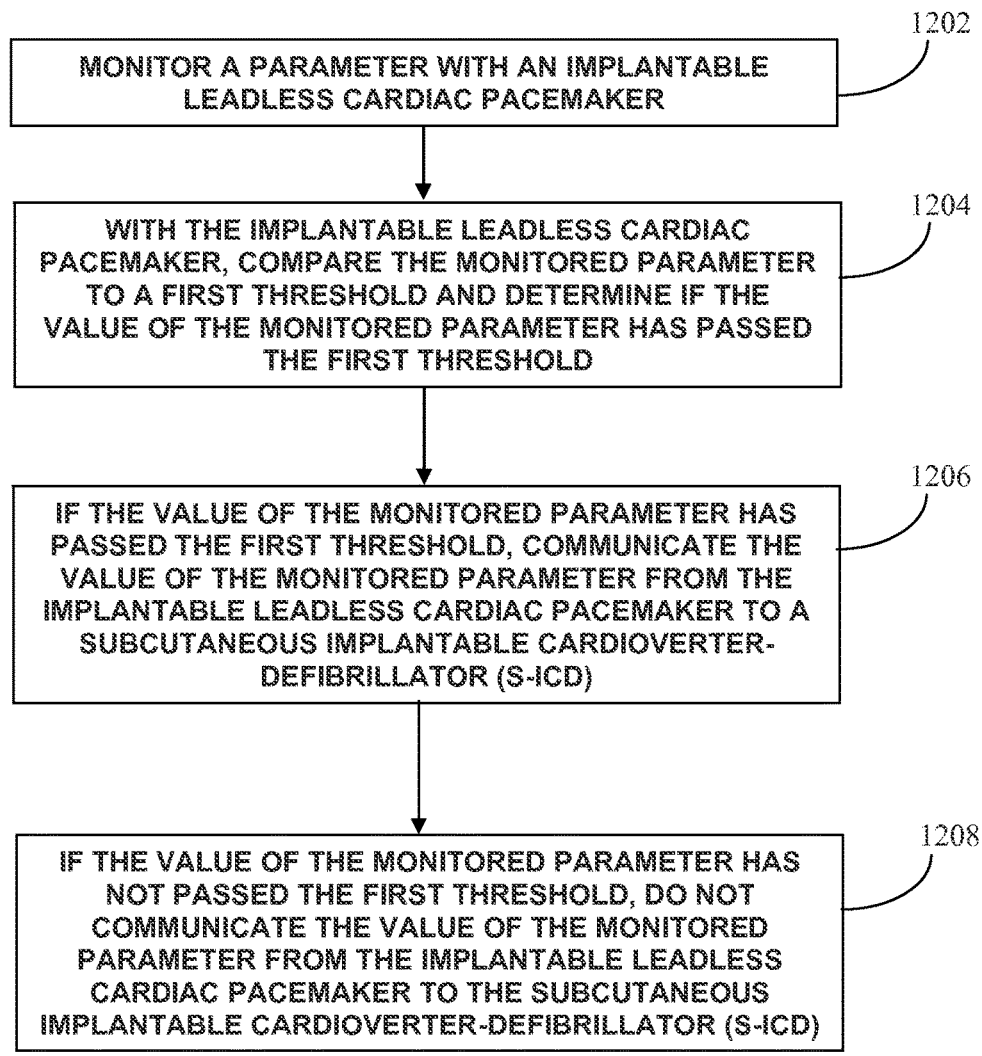
FIG. 12 is a flow diagram of an illustrative method that may be implemented by a medical device or medical device system, such as the illustrative medical devices and medical device systems described with respect to FIGS. 1-4.

FIG. 12 is a flow diagram of an illustrative method that may be implemented by an implantable medical device, such as shown in FIGS. 1 and 2, or a medical device system such as shown in FIGS. 3 and 4. Although the method of FIG. 12 will be described with respect to LCP 100, the illustrative method of FIG. 12 may be performed using any suitable medical device or medical device system.

According to the method depicted in FIG. 11, a first medical device may be implanted within a patient, such as if the first medical device is an ICP, an ICD, an S-ICD, or may be disposed in proximity to the patient, such as if the first medical device is an external medical device. The first medical device may be part of a medical device system along with a second medical device, such as LCP 100. In such a medical device system, LCP 100 may monitor a parameter, as shown at 1202. LCP 100 may further compare the monitored parameter to a first threshold and determine if the value of the monitored parameter has passed the first threshold, as shown at 1204. If the value of the monitored parameter has passed the first threshold, LCP 100 may communicate the value of the monitored parameter to a subcutaneous implantable cardioverter-defibrillator (S-ICD), as shown at 1206. If the value of the monitored parameter has not passed the first threshold, LCP 100 may not communicate the value of the monitored parameter to the subcutaneous implantable cardioverter-defibrillator (S-ICD), as shown at 1208.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A method of communicating information from a first medical device to a second medical device, the method comprising:

communicating a first threshold corresponding to a first physiological parameter of a patient from a first medical device to a second medical device, wherein the first medical device comprises a subcutaneous implantable cardioverter-defibrillator (S-ICD) with one or more electrodes configured to be adjacent the heart of the patient and the second medical device comprises a leadless pacemaker (LCP) that is configured to be implanted within the heart of the patient, the first physiological parameter is detected based at least in part on one or more of a cardiac electrical signal, a heart sound, and a motion signal;

monitoring a value of the first physiological parameter of the patient with the second medical device;

determining if the value of the first physiological parameter of the patient has passed the first threshold;

if the value of the first physiological parameter of the patient has passed the first threshold, communicating a first indication from the second medical device to the first medical device; and if the value of the first physiological parameter of the patient has not passed the first threshold, not communicating the first indication from the second medical device to the first medical device.

2. The method of claim 1, wherein the first indication comprises the value of the first physiological parameter.

3. The method of claim 1, wherein the first physiological parameter corresponds to one of a QRS width, an A-V interval, a V-V interval, and a T-wave amplitude.

4. The method of claim 1, further comprising:
after communicating the first indication from the second medical device to the first medical device, communicating a second threshold corresponding to the first physiological parameter of the patient from the first medical device to the second medical device, wherein the second threshold is different from the first threshold;
monitoring the value of the first physiological parameter of the patient with the second medical device; and
determining if the value of the first physiological parameter of the patient has passed the second threshold;
if the value of the first physiological parameter of the patient has passed the second threshold, communicating a second indication from the second medical device to the first medical device; and
if the value of the first physiological parameter of the patient has not passed the second threshold, not communicating the second indication from the second medical device to the first medical device.

5. The method of claim 4, wherein communicating the second threshold comprises communicating a new first threshold value from the first medical device to the second medical device.

6. The method of claim 4, wherein communicating the second threshold comprises communicating a delta value from the first medical device to the second medical device, wherein the second medical device adds the delta value to the first threshold to arrive at the second threshold.

7. The method of claim 1, further comprising:
communicating another threshold corresponding to a second physiological parameter of a patient from a first medical device to the second medical device;
monitoring a value of the second physiological parameter of the patient with the second medical device; and
determining if the value of the second physiological parameter of the patient has passed the another threshold;
if the value of the second physiological parameter of the patient has passed the another threshold, communicating another indication from the second medical device to the first medical device; and
if the value of the second physiological parameter of the patient has not passed the another threshold, not communicating the another indication from the second medical device to the first medical device.

8. The method of claim 1, further comprising:
after communicating the first indication from the second medical device to the first medical device, communicating an acknowledgement from the first medical device to the second medical device; and
if the second medical device does not receive the acknowledgement from the first medical device within a predetermined period of time, communicating the first indication from the second medical device to the first medical device again.

9. The method of claim 8, wherein the predetermined period of time is between two-hundred fifty milliseconds (250 ms) and one second (1 s).

10. A method of reducing communication transmissions in a medical device system, the method comprising:
monitoring a parameter with an implantable leadless cardiac pacemaker;
with the implantable leadless cardiac pacemaker, comparing the monitored parameter to a first threshold and determining if the value of the monitored parameter has passed the first threshold, the first parameter corresponding to one of a QRS width, an A-V interval, a V-V interval, or a T-wave amplitude;
if the value of the monitored parameter has passed the first threshold, communicating the value of the monitored parameter from the implantable leadless cardiac pacemaker to a subcutaneous implantable cardioverter-defibrillator (S-ICD); and
if the value of the monitored parameter has not passed the first threshold, not communicating the value of the monitored parameter from the implantable leadless cardiac pacemaker to the subcutaneous implantable cardioverter-defibrillator (S-ICD).

11. The method of claim 10, further comprising:
after receiving the value of the monitored parameter at the subcutaneous implantable cardioverter-defibrillator (S-ICD), communicating a second threshold from the subcutaneous implantable cardioverter-defibrillator (S-ICD) to the implantable leadless cardiac pacemaker, wherein the second threshold is different from the first threshold; and
if the value of the monitored parameter has passed the second threshold, communicating the value of the monitored parameter from the implantable leadless cardiac pacemaker to the subcutaneous implantable cardioverter-defibrillator (S-ICD); and
if the value of the monitored parameter has not passed the second threshold, not communicating the value of the monitored parameter from the implantable leadless cardiac pacemaker to the subcutaneous implantable cardioverter-defibrillator (S-ICD).

12. The method of claim 10, further comprising:
after communicating the value of the monitored parameter from the implantable leadless cardiac pacemaker to the subcutaneous implantable cardioverter-defibrillator (S-ICD), communicating an acknowledgement from the subcutaneous implantable cardioverter-defibrillator (S-ICD) to the implantable leadless cardiac pacemaker; and
if the implantable leadless cardiac pacemaker does not receive the acknowledgement from the subcutaneous implantable cardioverter-defibrillator (S-ICD) within a predetermined period of time, communicating the value of the monitored parameter from the implantable leadless cardiac pacemaker to the subcutaneous implantable cardioverter-defibrillator (S-ICD) again.

13. The method of claim 11, wherein the second threshold is further past the first threshold.

14. A method of communicating information from a first medical device to a second medical device, the method comprising:
communicating a first threshold corresponding to a first physiological parameter of a patient from a first medical device to a second medical device, wherein the first medical device comprises a subcutaneous implantable cardioverter-defibrillator (S-ICD) with one or more electrodes configured to be adjacent the heart of the patient and the second medical device comprises a leadless pacemaker (LCP) that is configured to be implanted within the heart of the patient;
monitoring a value of the first physiological parameter of the patient with the second medical device;

determining if the value of the first physiological parameter of the patient has passed the first threshold;

if the value of the first physiological parameter of the patient has passed the first threshold, communicating a first indication from the second medical device to the first medical device;

if the value of the first physiological parameter of the patient has not passed the first threshold, not communicating the first indication from the second medical device to the first medical device;

communicating a second threshold corresponding to the first physiological parameter of the patient from the first medical device to the second medical device, wherein the second threshold is further past the first threshold;

monitoring the value of the first physiological parameter of the patient with the second medical device;

determining if the value of the first physiological parameter of the patient has passed the second threshold;

if the value of the first physiological parameter of the patient has passed the second threshold, communicating a second indication from the second medical device to the first medical device; and if the value of the first physiological parameter of the patient has not passed the second threshold, not communicating the second indication from the second medical device to the first medical device.

15. The method of claim 14, wherein the first physiological parameter of the patient comprises a heart rate.

16. The method of claim 14, wherein the first physiological parameter of the patient corresponds to one of a QRS width, an A-V interval, a V-V interval, or a T-wave amplitude.

17. The method of claim 14, wherein the second threshold is communicated from the first medical device to the second medical device in response to the first medical device receiving the first indication from the second medical device.

* * * * *